US009295677B2

(12) United States Patent
Ling et al.

(10) Patent No.: US 9,295,677 B2
(45) Date of Patent: Mar. 29, 2016

(54) POLYHYDROXYLATED BILE ACIDS FOR TREATMENT OF BILIARY DISORDERS

(75) Inventors: Victor Ling, Vancouver (CA); Renxue Wang, Vancouver (CA); Jonathan Ahab Sheps, Vancouver (CA)

(73) Assignee: Qing Bile Therapeutics Inc., Vancouver (CA)

( * ) Notice: Subject to any disclaimer, the term of this patent is extended or adjusted under 35 U.S.C. 154(b) by 20 days.

(21) Appl. No.: 13/406,092

(22) Filed: Feb. 27, 2012

(65) Prior Publication Data

US 2012/0277198 A1 Nov. 1, 2012

Related U.S. Application Data

(63) Continuation of application No. PCT/CA2010/001338, filed on Aug. 25, 2010, and a continuation-in-part of application No. 12/919,381, filed as application No. PCT/CA2009/000257 on Feb. 26, 2009, now abandoned.

(60) Provisional application No. 61/236,750, filed on Aug. 25, 2009, provisional application No. 61/064,280, filed on Feb. 26, 2008.

(51) Int. Cl.
*A61K 31/575* (2006.01)
*A61K 47/48* (2006.01)
*C07J 9/00* (2006.01)
*C07J 41/00* (2006.01)

(52) U.S. Cl.
CPC ......... *A61K 31/575* (2013.01); *A61K 47/48023* (2013.01); *C07J 9/005* (2013.01); *C07J 41/0061* (2013.01)

(58) Field of Classification Search
CPC ..... A61K 31/575; C07J 9/005; C07J 41/0061
See application file for complete search history.

(56) References Cited

U.S. PATENT DOCUMENTS

| 5,955,456 A * | 9/1999 | Prato et al. ..................... 514/182 |
| 2002/0031558 A1 | 3/2002 | Yoo |
| 2009/0074895 A1 | 3/2009 | Mikov et al. |

FOREIGN PATENT DOCUMENTS

| EP | 0489933 A1 * | 1/1992 | ................. C07J 9/00 |
| JP | 63-2932 | 1/1988 | |
| JP | 2002-522357 A | 7/2002 | |
| WO | WO 2006/116814 A1 * | 11/2006 | ............. A61K 36/28 |
| WO | WO-2006/116814 A1 | 11/2006 | |
| WO | WO-2006/116815 A1 | 11/2006 | |
| WO | WO-2009/105897 A1 | 9/2009 | |

OTHER PUBLICATIONS

Gong et al 'Ursodexoycholic Acid for Patients With Primary Biliary Cirrhosis: An Updated Systematic Review and Meta-Analysis of Randomized Clinical Trials Using Bayesian Approach as Sensitivity Analyses' American Journal of Gastroenterology, vol. 102, p. 1799-1807, 2007.*
Aggarwal et al., "Synthesis of 3alpha,6beta,7alpha,12beta- and 3alpha,6beta,7beta,12beta-tetrahydroxy-5beta-cholanoic acids," Steroids 57:107-111 (1992).
Asamoto et al., "Bile-salt hydrophobicity is a key factor regulating rat liver plasma-membrane communication: relation to bilayer structure, fluidity and transporter expression and function," Biochem J. 359:605-610 (2001).
Böhme et al., "Cholestasis caused by inhibition of the adenosine triphosphate-dependent bile salt transport in rat liver," Gastroenterology. 107(1):255-265 (1994).
Byrne et al., "The human bile salt export pump: characterization of substrate specificity and identification of inhibitors," Gastroenterology. 123(5):1649-1658 (2002).
Chen et al., "Developmental expression of canalicular transporter genes in human liver," J Hepatol. 43:472-477 (2005).
Chen et al., "Progressive familial intrahepatic cholestasis with high gamma-glutamyltranspeptidase levels in Taiwanese infants: role of MDR3 gene defect?," Pediatr Res. 50(1):50-55 (2001).
Chiang et al., "Farnesoid X receptor responds to bile acids and represses cholesterol 7alpha-hydroxylase gene (CYP7A1) transcription," J Biol Chem. 275(15):10918-10924 (2000).
Childs et al., The MDR Superfamily of Genes and Its Biological Implications. *Important Advances in Oncology*. ed. DeVita et al., Philadelphia: J.B. Lippincott Company, 21-36 (1994).
Database Caplus [Online] Chemical Abstracts Service, Columbus, Ohio, US; Sato, Norihito et al.: The characterization of relationship between chemical structure of bile acids and recognition properties by canalicular bile acid transporter (cbat)", XP002689934, retrieved from STN, Database accession No. 1999:362525; & Sato, Norihito et al.: The characterization of relationship between chemical structure of bile acids and recognition properties by canalicular bile acid transporter (cbat)", Yakuri to Chiryo, vol. 27, No. suppl. 3, 1999, pp. 941-947, ISSN: 0386-3603.
Database WPI, Week 198807, Thomson Scientific, London, GB; AN 1988-045809, XP002689933-& JP 63 002932 A (Teijin Ltd) Jan. 7, 1988.
Fattinger et al., "The endothelin antagonist bosentan inhibits the canalicular bile salt export pump: a potential mechanism for hepatic adverse reactions," Clin Pharmacol Ther. 69(4):223-231 (2001).
Fieser et al., "Synthesis of naphthoquinones for studies of the inhibition of enzyme systems," J Am Chem Soc. 71:3609-3614 (1949).
Forrest, Dana Nichole, Thesis: "Bile salt hydroxylation as a mechanism for detoxification in spgp knockout mice," M.Sc., University of British Columbia, 2003.
Funk et al., "Cholestatic potential of troglitazone as a possible factor contributing to troglitazone-induced hepatotoxicity: in vivo and in vitro interaction at the canalicular bile salt export pump (Bsep) in the rat," Mol Pharmacol. 59(3):627-635 (2001).
Funk et al., "Troglitazone-induced intrahepatic cholestasis by an interference with the hepatobiliary export of bile acids in male and female rats. Correlation with the gender difference in troglitazone sulfate formation and the inhibition of the canalicular bile salt export pump (Bsep) by troglitazone and troglitazone sulfate," Toxicology. 167:83-98 (2001).

(Continued)

Primary Examiner — Wu-Cheng Winston Shen
Assistant Examiner — Christopher R Stone
(74) Attorney, Agent, or Firm — Clark & Elbing LLP

(57) ABSTRACT

The invention provides, in part, polyhydroxylated bile acids for treating biliary disorders, for example, biliary disorders arising out of cholestasis of portal hypertension. The invention also provides, in part, polyhydroxylated bile acids for stimulating bile flow. New compounds 2α,3α,7α,12α-tetrahydroxy-5β-cholanoic acid and 3α.4α,7α,12α-tetrahydroxy-5β-cholanoic acid are disclosed, uses thereof and synthesis thereof.

18 Claims, 13 Drawing Sheets

(56) References Cited

OTHER PUBLICATIONS

Gerloff et al., "The sister of P-glycoprotein represents the canalicular bile salt export pump of mammalian liver," J Biol Chem. 273(16):10046-10050 (1998).

Gerloff et al., "Taurocholate induces preferential release of phosphatidylcholine from rat liver canalicular vesicles," Liver. 18:306-312 (1998).

Goodwin et al., "A regulatory cascade of the nuclear receptors FXR, SHP-1, and LRH-1 represses bile acid biosynthesis," Mol Cell. 6:517-526 (2000).

Gouin et al., "Synthesis of 3alpha- and 3beta-dimers from selected bile acids," Steroids. 61:664-669 (1996).

Green et al., "Molecular cloning and characterization of the murine bile salt export pump," Gene. 241:117-123 (2000).

Hagey et al., "An N-acyl glycyltaurine conjugate of deoxycholic acid in the biliary bile acids of the rabbit," J Lipid Res. 39:2119-2124 (1998).

Hofmann, "Bile secretion in mice and men," Hepatology. 34(4):848-850 (2001).

Hofmann, "Defective biliary secretion during total parenteral nutrition: probable mechanisms and possible solutions," J Pediatr Gastroenterol Nutr. 20(4):376-390 (1995).

Hofmann, "The continuing importance of bile acids in liver and intestinal disease," Arch Intern Med. 159:2647-2658 (1999).

Hofmann et al., "A proposed nomenclature for bile acids," J Lipid Res. 33:599-604 (1992).

Iida et al., "Potential bile acid metabolites. 16. Synthesis of stereoisomeric 3alpha,6,7,12alpha-tetrahydroxy-5beta-cholanoic acids," Steroids. 55:530-539 (1990).

Iida et al., "Potential bile acid metabolites. 17. Synthesis of 2beta-hydroxylated bile acids," Steroids. 56:114-122 (1991).

Iida et al., "Potential bile acid metabolites. XVIII. Synthesis of stereoisomeric 3,6,12alpha-trihydroxy-5beta-cholanoic acids," J Lipid Res. 32:649-658 (1991).

Iida et al., "Potential bile acid metabolites. 19. The epimeric 3alpha,6,7beta-trihydroxy- and 3alpha,6,7beta,12alpha-tetrahydroxy-5alpha-cholanoic acids," Steroids. 58:148-152 (1993).

Iida et al., "Potential bile acid metabolites. 25. Synthesis and chemical properties of stereoisomeric 3alpha,7alpha,16- and 3alpha,7alpha,15-trihydroxy-5beta-cholan-24-oic acids," Chem Pharm Bull. 50(10):1327-1334 (2002).

Iida et al., "Preparation of glycine-conjugated bile acids and their gas/liquid chromatographic analysis on an aluminum-clad flexible fused silica capillary column," Biomed Chromatogr. 6:4-8 (1992).

Jacquemin, "Progressive familial intrahepatic cholestasis: Genetic basis and treatment," Clin Liver Dis. 4(4):753-763 (2000).

Jansen et al., "Genetic cholestasis, causes and consequences for hepatobiliary transport," Liver Int. 23:315-322 (2003).

Jansen et al., "Hepatocanalicular bile salt export pump deficiency in patients with progressive familial intrahepatic cholestasis," Gastroenterology. 117(6):1370-1379 (1999).

Jones et al., "Bile salt-induced apoptosis of hepatocytes involves activation of protein kinase C," Am J Physiol Gastrointest Liver Physiol. 272:G1109-G1115 (1997).

Kakiyama et al., "Chemical synthesis of (22E)-3alpha, 6beta, 7beta-trihydroxy-5beta-chol-22-en-24-oic acid and its taurine and glycine conjugates: a major bile acid in the rat," J Lipid Res. 45:567-573 (2004).

Keitel et al., "Combined mutations of canalicular transporter proteins cause severe intrahepatic cholestasis of pregnancy," Gastroenterology. 131(2):624-629 (2006).

Kihira et al., "Synthesis of new bile salt analogues, sodium 3alpha, 7alpha-dihydroxy-5beta-cholane-24-sulfonate and sodium 3alpha,7beta-dihydroxy-5beta-cholane-24-sulfonate," J Lipid Res. 31:1323-1326 (1990).

Knisely, "Progressive familial intrahepatic cholestasis: A personal perspective," Pediatr Dev Pathol. 3:113-125 (2000).

Kubitz et al., "Benign recurrent intrahepatic cholestasis associated with mutations of the bile salt export pump," J Clin Gastroenterol. 40(2):81-85 (2006).

Kurosawa et al., "Synthesis of 3alpha,7alpha,12alpha-trihydroxy- and 3alpha,7alpha-dihydroxy-5beta-cholestan-26-oic acids by the use of beta-ketosulfoxide," Steroids. 60:439-444 (1995).

Kurosawa et al., "Synthesis of diastereomers of 3alpha,7alpha,12alpha,24-tetrahydroxy- and 3alpha,7alpha,24-trihydroxy-5beta-cholestan-26-oic acids and their structures," Steroids. 61:421-428 (1996).

Kwo et al., "Nuclear serine protease activity contributes to bile acid-induced apoptosis in hepatocytes," Am J Physiol Gastrointest Liver Physiol. 268:G613-G621 (1995).

Lam et al., "Bile acid transport in sister of P-Glycoprotein (ABCB11) knockout mice," Biochemistry. 44:12598-12605 (2005).

Lam et al., "Bile acid transport in Spgp (Bsep) knockout mice," In Falk Symposium No. 141. XVIII International Bile Acid Meeting: Bile Acid Biology and its Therapeutic Implications (Kluwer Academic, Dordrecht), 91-100 (2004).

Leppik, "Improved synthesis of 3-keto, 4-ene-3-keto, and 4,6-diene-3-keto bile acids," Steroids. 41(4):475-484 (1983).

Makishima et al., "Identification of a nuclear receptor for bile acids," Science. 284:1362-1365 (1999).

Matoba et al., "Synthesis of new bile acid analogues and their metabolism in the hamster: 3alpha, 6alpha-dihydroxy-6beta-methyl-5beta-cholanoic acid and 3alpha, 6beta-dihydroxy-6alpha-methyl-5beta-cholanoic acid," J Lipid Res. 30:1005-1014 (1989).

Nakagawa et al., "Bile acid metabolism in early life: studies of amniotic fluid," J Lipid Res. 31:1089-1098 (1990).

Narasimhan et al., "Synthetic applications of zinc borohydride," Aldrichimica Acta. 31(1):19-26 (1998).

Noé et al., "Functional expression of the canalicular bile salt export pump of human liver," Gastroenterology. 123(50:1659-1666 (2002).

Ornstein et al., "Syntheses of 6-oxodecahydroisoquinoline-3-carboxylates. Useful intermediates for the preparation of conformationally defined excitatory amino acid antagonists," J Org Chem. 56:4388-4392 (1991).

Parks et al., "Bile acids: natural ligands for an orphan nuclear receptor," Science. 284:1365-1368 (1999).

Pütz et al., "Synthesis of phospholipid-conjugated bile salts and interaction of bile salt-coated liposomes with cultured hepatocytes," J Lipid Res. 46:2325-2338 (2005).

Rodrigues et al., "A novel role for ursodeoxycholic acid in inhibiting apoptosis by modulating mitochondrial membrane perturbation," J Clin Invest. 101(12):2790-2799 (1998).

Rossi et al., "High pressure liquid chromatographic analysis of conjugated bile acids in human bile: simultaneous resolution of sulfated and unsulfated lithocholyl amidates and the common conjugated bile acids," J Lipid Res. 28:589-595 (1987).

Rust et al., "The bile acid taurochenodeoxycholate activates a phosphatidylinositol 3-kinase-dependent survival signaling cascade," J Biol Chem. 275(26):20210-20216 (2000).

Schinkel et al., "Normal viability and altered pharmacokinetics in mice lacking mdr1-type (drug-transporting) P-glycoproteins," Proc Natl Acad Sci USA. 94:4028-4033 (1997) (Correction included).

Shapiro et al., "P-glycoprotein-mediated Hoechst 33342 transport out of the lipid bilayer," Eur J Biochem. 250:115-121 (1997).

Shapiro et al., "Positively cooperative sites for drug transport by P-glycoprotein with distinct drug specificities," Eur J Biochem. 250:130-137 (1997).

Shapiro et al., "Stimulation of P-glycoprotein-mediated drug transport by prazosin and progesterone: Evidence for a third drug-binding site," Eur J Biochem. 259:841-850 (1999).

Sinal et al., "Targeted disruption of the nuclear receptor FXR/BAR impairs bile acid and lipid homeostasis," Cell. 102:731-744 (2000).

Sodeman et al., "Bile salts mediate hepatocyte apoptosis by increasing cell surface trafficking of Fas," Am J Physiol Gastrointest Liver Physiol. 278:G992-G999 (2000).

Stieger et al., "ATP-dependent bile-salt transport in canalicular rat liver plasma-membrane vesicles," Biochem J. 284:67-74 (1992).

Stieger et al., "Drug- and estrogen-induced cholestasis through inhibition of the hepatocellular bile salt export pump (Bsep) of rat liver," Gastroenterology 118:422-430 (2000).

Strautnieks et al., "A gene encoding a liver-specific ABC transporter is mutated in progressive familial intrahepatic cholestasis," Nature Genetics 20:233-238 (1998).

(56) References Cited

OTHER PUBLICATIONS

Takikawa et al., "Effect of tauro-alpha-muricholate and tauro-beta-muricholate on oestradiol-17beta-glucuronide-induced cholestasis in rats," J Gastroenterol Hepatol. 12:84-86 (1997).
Tohma et al., "Synthesis of the 1beta-hydroxylated bile acids and identification of 1beta,3alpha,7alpha-trihydroxy- and 1beta,3alpha,7alpha,12alpha-tetrahydroxy-5beta-cholan-24-oic acids in human meconium," Chem Pharm Bull 33(7):3071-3073 (1985).
Tserng et al., "Formylated bile acids: Improved synthesis, properties, and partial deformylation," Steroids. 29(5):635-648 (1977).
Tsukada et al., "Isolation of the bile canalicular actin-myosin II motor," Proc Natl Acad Sci USA. 91:6919-6923 (1994).
Vallejo et al., "Potential role of trans-inhibition of the bile salt export pump by progesterone metabolites in the etiopathogenesis of intrahepatic cholestasis of pregnancy," J Hepatol. 44:1150-1157 (2006).
van Mil et al., "FIC1 disease: A spectrum of intrahepatic cholestatic disorders," Semin Liver Dis. 21(4):535-544 (2001).
Wang et al., "Compensatory role of P-glycoproteins in knockout mice lacking the bile salt export pump," Hepatology 50(3):948-956 (2009).
Wang et al., "Endogenous bile acids are ligands for the nuclear receptor FXR/BAR," Molecular Cell. 3:543-553 (1999).
Wang et al., "Severe cholestasis induced by cholic acid feeding in knockout mice of sister of P-glycoprotein," Hepatology. 38(6):1489-1499 (2003).
Wang et al., "Targeted inactivation of sister of P-glycoprotein gene (spgp) in mice results in nonprogressive but persistent intrahepatic cholestasis," Proc Natl Acad Sci USA 98(4):2011-2016 (2001).
Extended European Search Report for European Application No. 10811080.0, completed Jan. 11, 2013 (15 pages).
International Preliminary Report on Patentability for International Application No. PCT/CA2009/000257, issued Aug. 31, 2010 (8 pages).
International Preliminary Report on Patentability for International Application No. PCT/CA2010/001338, mailed Mar. 8, 2012 (8 pages).
International Search Report and Written Opinion for International Application No. PCT/CA2009/000257, mailed Jun. 18, 2009 (12 pages).
International Search Report and Written Opinion for International Application No. PCT/CA2010/001338, mailed Nov. 25, 2010 (12 pages).
Hagey et al., "Evolutionary diversity of bile salts in reptiles and mammals, including analysis of ancient human and extinct giant ground sloth coprolites," BMC Evol Biol. 10:133 (2010) (23 pages).
Palmer et al., "Hypercholeresis induced by norchenodeoxycholate in biliary fistula rodent," Am J Physiol Gastrointest Liver Physiol. 252(2 Pt 1):G219-28 (1987).
Roda et al., "Bile acid structure-activity relationship: evaluation of bile acid lipophilicity using 1-octanol/water partition coefficient and reverese phase HPLC," J Lipid Res 31(8):1433-43 (1990).
Wang et al., "Defective canalicular transport and toxicity of dietary ursodeoxycholic acid in the *abcb11-/-* mouse: transport and gene expression studies," Am J Physiol Gastrointest Liver Physiol. 305(4):G286-94 (2013) (33 pages).
Singapore Search Report and Written Opinion for Singapore Application No. 201201313-2, dated May 23, 2013 (20 pages).
Office Action for Japanese Application No. 2012-525830, mailed Aug. 27, 2014 (5 pages).
Perwaiz et al., "Appearance of atypical 3 alpha,6 beta,7 beta,12 alpha-tetrahydroxy-5 beta-cholan-24-oic acid in spgp knockout mice," J Lipid Res. 44(3):494-502 (2003).
Sato et al., "The characterization of relationship between chemical structure of bile acids and recognition properties by canalicular bile acid transporter (cbat)," Jpn Pharmacol Ther. 27(suppl. 3):S941-S947 (1999) (English abstract included).
Seelig, "A general pattern for substrate recognition by P-glycoprotein," Eur J Biochem. 251(1-2):252-61 (1998).
Second Office Action for Chinese Application No. 2010800483149, issued Oct. 9, 2014 (8 pages).
Communication pursuant to Article 94(3) EPC for European Application No. 10811080.0, mailed Mar. 27, 2014 (10 pages).
Office Action for Chinese Application No. 201080048314.9, mailed Jan. 28, 2014 (11 pages).
Search and Examination Report for Singapore Application No. 201201313-2, mailed Feb. 7, 2014 (12 pages).
First Examination Report for Australian Application No. 2010286253, issued Oct. 31, 2014 (4 pages).
Bari et al., "Ezetimibe: its novel effects on the prevention and the treatment of cholesterol gallstones and nonalcoholic Fatty liver disease," J Lipids. 2012:302847 (2012) (16 pages).
Geenes et al., "Intrahepatic cholestasis of pregnancy," World J Gastroenterol. 15(17):2049-66 (2009).
Portincasa et al., "Therapy of gallstone disease: What it was, what it is, what it will be," World J Gastrointest Pharmacol Ther. 3(2):7-20 (2012).
Zhu et al., "Network meta-analysis of randomized controlled trials: efficacy and safety of UDCA-based therapies in primary biliary cirrhosis," Medicine (Baltimore). 94(11):e609 (2015) (9 pages).
Office Action for Chinese Application No. 201080048314.9, dated Apr. 3, 2015 (3 pages).
Communication pursuant to Article 94(3) EPC for European Patent Application No. 10811080.0 dated Jul. 6, 2015 (7 pages).
Official Action for Japanese Patent Application No. 2012-525830, dated Jun. 3, 2015 (6 pages) (English translation of pertinent parts of the Official Action included).
Fourth Office Action for Chinese Application No. 201080048314.9, dated Oct. 10, 2015 (7 pages).

\* cited by examiner

FIG. 12
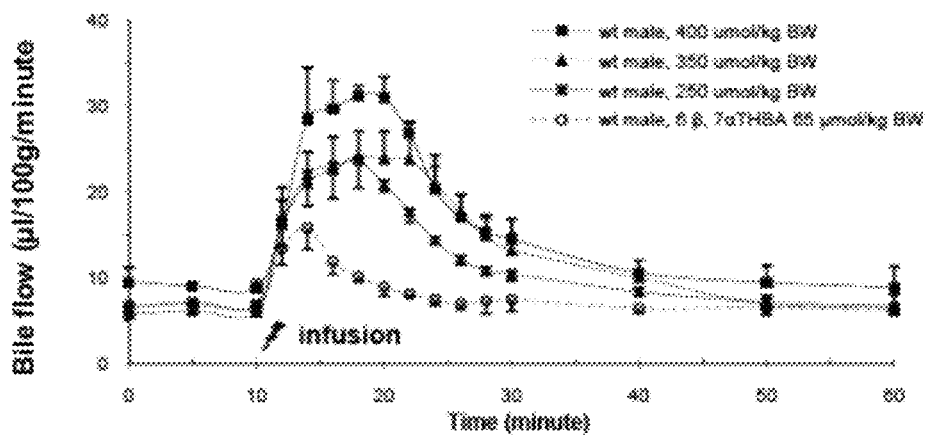
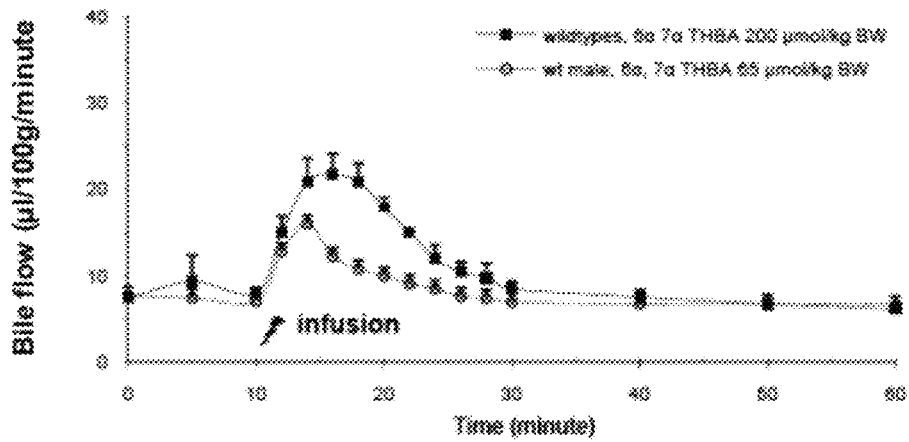
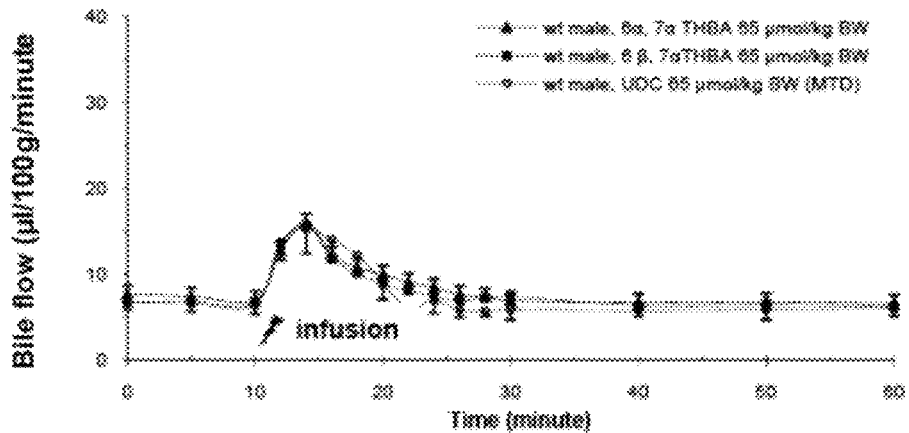

SEQUENCE LISTING

```
<160> NUMBER OF SEQ ID NOS: 7

<210> SEQ ID NO 1
<211> LENGTH: 19
<212> TYPE: DNA
<213> ORGANISM: Artificial Sequence
<220> FEATURE:
<223> OTHER INFORMATION: Sense Primer

<400> SEQUENCE: 1
cacgaaccac ggcactgtt                                               19

<210> SEQ ID NO 2
<211> LENGTH: 22
<212> TYPE: DNA
<213> ORGANISM: Artificial Sequence
<220> FEATURE:
<223> OTHER INFORMATION: Anti-sense primer

<400> SEQUENCE: 2
ttttcttgct gccagtctgg ac                                           22

<210> SEQ ID NO 3
<211> LENGTH: 25
<212> TYPE: DNA
<213> ORGANISM: Artificial Sequence
<220> FEATURE:
<223> OTHER INFORMATION: Probe

<400> SEQUENCE: 3
tgtgcacagg agccaagagt gaaga                                        25

<210> SEQ ID NO 4
<211> LENGTH: 135
<212> TYPE: DNA
<213> ORGANISM: Mus musculus

<400> SEQUENCE: 4
atggagtttg aagagaacct taagggaaga gcagacaaga acttctcgaa gatgggcaaa    60
```

```
aagagtaaaa aggagaagaa agaaaagaaa cctgctgttg gcgtatttgg gatggtggac    120
ccaacagtac tctga                                                    135

<210> SEQ ID NO 5
<211> LENGTH: 44
<212> TYPE: PRT
<213> ORGANISM: Mus musculus

<400> SEQUENCE: 5

Met Glu Phe Glu Glu Asn Leu Lys Gly Arg Ala Asp Lys Asn Phe Ser
1               5                   10                  15

Lys Met Gly Lys Lys Ser Lys Lys Glu Lys Glu Lys Pro Ala
            20                  25                  30

Val Gly Val Phe Gly Met Val Asp Pro Thr Val Leu
        35                  40

<210> SEQ ID NO 6
<211> LENGTH: 153
<212> TYPE: DNA
<213> ORGANISM: Mus musculus

<400> SEQUENCE: 6
atggagtttg aagagaacct taagggaaga gcagacaaga acttctcgaa gatgggcaaa    60
aagagtaaaa aggagaagaa agaaaagaaa cctgctgttg gcgtatttgg gatggaattg    120
gtgacaaaat tgggatgttt tttcagtcca taa                                153

<210> SEQ ID NO 7
<211> LENGTH: 50
<212> TYPE: PRT
<213> ORGANISM: Mus musculus

<400> SEQUENCE: 7

Met Glu Phe Glu Glu Asn Leu Lys Gly Arg Ala Asp Lys Asn Phe Ser
1               5                   10                  15

Lys Met Gly Lys Lys Ser Lys Lys Glu Lys Glu Lys Pro Ala
            20                  25                  30

Val Gly Val Phe Gly Met Glu Leu Val Thr Lys Leu Gly Cys Phe Phe
        35                  40                  45

Ser Pro
    50
```

POLYHYDROXYLATED BILE ACIDS FOR TREATMENT OF BILIARY DISORDERS

CROSS-REFERENCE TO RELATED APPLICATIONS

This application is a continuation of International Patent Application No. PCT/CA2010/001338, filed Aug. 25, 2010, which claims benefit of U.S. Provisional Patent Application No. 61/236,750, filed Aug. 25, 2009. This application is also a continuation-in-part of U.S. application Ser. No. 12/919,381, filed Aug. 25, 2010, which was a U.S. national phase entry of International Application No. PCT/CA2009/000257, filed Feb. 26, 2009, which claims benefit of U.S. Provisional Patent Application No. 61/064,280, filed Feb. 26, 2008.

FIELD OF INVENTION

The present invention provides polyhydroxylated bile acids and derivatives thereof to treat biliary disorders or stimulate bile flow. More specifically, the present invention provides polyhydroxylated bile acids and derivatives thereof to treat biliary disorders leading to, or associated with, cholestasis or portal hypertension, or to stimulate bile flow.

BACKGROUND OF THE INVENTION

Bile is a complex secretion produced by the liver. It is stored in the gall bladder and periodically released into the small intestine to aid in digestion. Bile components include cholesterol, phospholipids, bile pigments, and various toxins that the liver eliminates through biliary/fecal exclusion. Bile salts are synthesized and actively secreted across canalicular membranes providing the osmotic force to drive the flow of bile. This is the rate-limiting step for bile formation. Bile flow is essential for liver detoxification, digestion, cholesterol metabolism, and absorption of lipid-soluble nutrients and vitamins.

Bile acids are critical as carriers for elimination of cholesterol from the body through biliary secretion and as a detergent for the ingestion of fatty acids and fat-soluble vitamins (23). Bile acids also play important roles in regulating cell apoptosis/survival (37; 38; 39; 40; 41) and in regulating gene expression through the farnesoid X-activated receptor (42; 43; 44; 45; 46; 47) in hepatocytes. Bile acids are synthesized in hepatocytes from cholesterol, secreted into the bile after being conjugated with glycine or taurine, reabsorbed in the small intestine, and recirculated back to hepatocytes through the portal vein. Canalicular secretion of bile acids from liver into the bile is a key process in the enterohepatic circulation of bile acids and its malfunction results in different hepatic diseases (23). If this process is disrupted, accumulation of bile acids often causes liver damage due to detergent effects. In humans, the bile acid pool circulates 6-10 times every 24 h, resulting in daily bile salt secretion of 20-40 g in about 400 ml (51; 49).

Common bile acids found in the bile of selected mammals include the following:

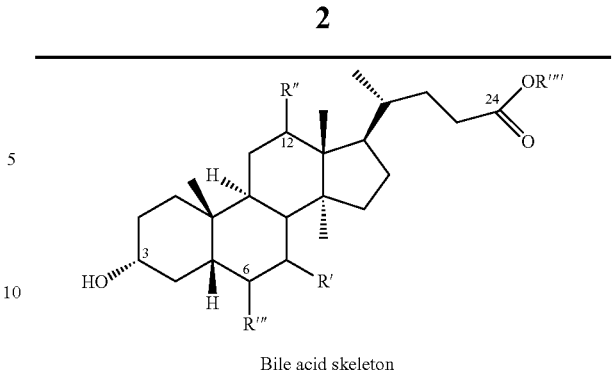

Bile acid skeleton

| Common Name | R' | R" | R'" | Commonly found in species |
|---|---|---|---|---|
| Cholic acid (3α7α12) | α-OH | α-OH | H | bear, cat, hamster, human, mouse, pig, rabbit, rat |
| Chenodeoxycholic acid (3α7α) | α-OH | H | H | bear, hamster, human, pig |
| Deoxycholic acid (3α12α) | H | α-OH | H | cat, human, rabbit |
| Ursodeoxycholic acid (3α7β) | β-OH | H | H | bear |
| Lithocholic acid (3α) | H | H | H | human, rat, mouse |
| β-muricholic acid (3α6β7β) | β-OH | H | β-OH | mouse, rat |
| α-muricholic acid (3α6α7β) | α-OH | H | β-OH | pig, mouse, rat |
| Ω-muricholic acid (3α6α7α) | β-OH | H | α-OH | mouse, rat |

R""-taurine or glycine

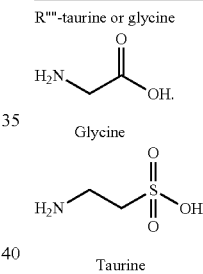

Glycine

Taurine

Bile Salt Export Protein (BSEP, ABCB11, or Sister of P-glycoprotein (SPGP)), a bile canalicular ATP-binding cassette (ABC) protein, has been identified as the main transport system for the biliary secretion of bile acids (50; 13). BSEP mutations in humans lead to impaired bile salt secretion and a severe liver disease, progressive familial intrahepatic cholestasis type 2 (PFIC2) (1, 2). Bile acid secretion in PFIC2 patients is usually less than 1% of normal (2). BSEP has also been implicated as being a target for drugs that cause cholestasis (3-6). BSEP mutations have also been associated with chronic intrahepatic cholestasis, benign recurrent intrahepatic cholestasis type 2 (BRIC 2) (7, 8) and Intrahepatic Cholestasis of Pregnancy (9, 10). Mouse Bsep transports bile acids in the order of preference: taurochenodeoxycholate>tauroursodeoxycholate= taurocholate>glycocholate=cholate (11-16). Rat liver plasma membrane vesicles exhibit similar preference (17). The bile acid preferences and activity of BSEP are similar among human, rat and mouse.

bsep knockout (KO) mice suffer a cholestatic illness with increased mortality in pups, decreased fertility in adults, and bile flow only ¼ of normal amounts (18). Residual bile flow in bsep KO mice is greater than that of PFIC2 patients, and the phenotype less severe, in that bsep KO mice can survive infancy and have a normal lifespan (18). The livers of bsep KO mice express elevated levels of P-glycoprotein (Mdr1a/1b) and their bile contains novel species of bile acid, including tetrahydroxylated bile acids (THBAs) not normally present in mouse or human bile (16, 18). When fed a diet of 0.5% cholate the bsep KO mice become severely cholestatic but at the same time secrete a large amount of bile salt into the bile. To explain this apparently contradictory result, a 'rain barrel' model was proposed, suggesting the containment level of bile salt in hepatocytes depends on both the affinity of the transporter for bile acids ($K_m$) and the rate of bile acid output (19). The bsep KO mice exhibit severe cholestasis on a cholate-enriched diet, since their high bile flow rate and bile acid output is mediated by a transporter whose $K_m$ is not low enough to reduce accumulated intrahepatic bile salt below toxic levels. The rain barrel model predicts that the alternative bile salt transporter has a lower affinity for cholate than BSEP.

When plasma membrane vesicles from the hamster B30 cell line, containing a high level of P-glycoprotein (Mdr1, Abcb1a) were examined, ATP-dependent taurocholate transport (20) with a $K_m$ of 69 μM, about seven-fold higher than Bsep was observed, suggesting P-glycoprotein transports taurocholate with a relatively low affinity. Analysis of biliary bile salt composition in bsep KO mice indicates that P-glycoprotein favours the less hydrophobic muricholates and THBAs over the more hydrophobic primary bile acids in both human and mouse (18, 21). This may explain the differing severity of the cholestatic phenotypes in bsep KO mice and PFIC2 in humans. In the bsep KO mice, murine P-glycoprotein transports intrahepatic muricholate and THBAs, across the canalicular membranes to maintain nearly normal bile flow, resulting in a mild phenotype. Since humans do not normally synthesize muricholate or THBAs, this option is not available to human MDR1 and results in the severe cholestasis of PFIC2 where bile flow diminishes to 1% of normal (2).

Upregulated Mdr1a/1b expression (16, 20) in the bsep knockout mice, and the known functional redundancy of the ABCB/P-glycoprotein family suggested a role for Mdr1 in mediating bile flow. However, while the bsep knockout mice exhibit very mild cholestasis throughout life, mdr1a$^{-/-}$/mdr1b$^{-/-}$ double knockout mice are healthy, with no obvious phenotype, though they do have specific defects in biliary excretion of infused drugs that are known to be Mdr1 substrates (22).

Some cholestatic conditions, such as Primary Biliary Cirrhosis, are treated by to supplementation with a low-toxicity bile acid not normally found in human bile, ursodeoxycholate. Dietary supplementation with ursodeoxycholate did not result in greater bile flow in bsep KO mice and may even have been toxic, suggesting that BSEP is responsible for the bulk of natural ursodeoxycholate transport, and so ursodeoxycholate may not help PFIC2 patients or anyone else suffering from a BSEP insufficiency, whether inherited, associated with pregnancy, or resulting from adverse drug or dietary exposures.

SUMMARY OF THE INVENTION

The invention provides, in part, polyhydroxylated bile acids for treating biliary disorders, for example, biliary disorders arising out of cholestasis or portal hypertension, or for stimulating bile flow in for example normal subjects or subjects not diagnosed with a biliary disorder.

In one aspect, the invention provides a method of treating a bile disorder in a subject in need thereof or of stimulating bile flow in a subject, the method comprising administering an effective amount of a compound according to Formula I:

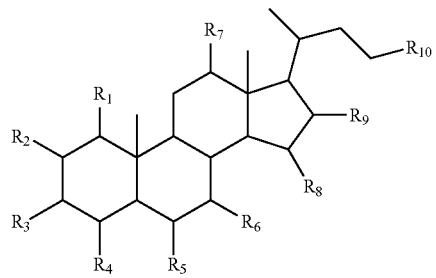

or a derivative thereof, wherein any one of $R_1$ to $R_9$ may be —H or —OH, provided that at least four of $R_1$ to $R_9$ are —OH; and $R_{10}$ may be —COOH or —CH$_2$OH.

In an alternative aspect, the invention provides a pharmaceutical or nutritional composition comprising a compound according to Formula I:

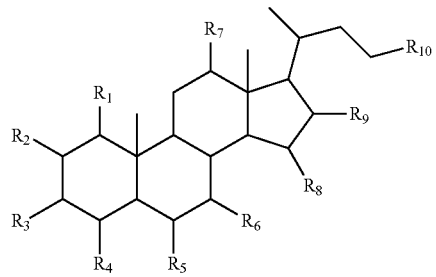

or a derivative thereof, together with a pharmaceutically or physiologically or nutritionally acceptable carrier, wherein any one of $R_1$ to $R_9$ may be —H or —OH, provided that at least four of $R_1$ to $R_9$ are —OH; and $R_{10}$ may be —COOH or —CH$_2$OH.

In an alternative aspect, the invention provides the use of a pharmaceutical or nutritional composition according to the invention for the preparation of a medicament for treating a biliary disorder or stimulating bile flow.

In an alternative aspect, the invention provides an article of manufacture comprising a compound according to Formula I:

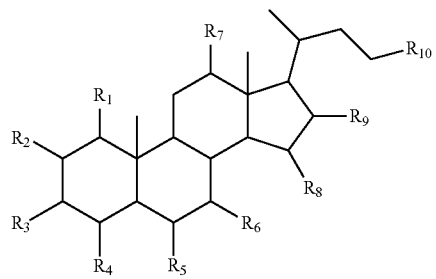

or a derivative thereof, together with instructions for use in treating a biliary disorder or stimulating bile flow, wherein any one of $R_1$ to $R_9$ may be —H or —OH, provided that at least four of $R_1$ to $R_9$ are —OH; and $R_{10}$ may be —COOH or —CH$_2$OH.

In alternative embodiments, the compound comprises a hydrophilicity greater than that of cholate.

In alternative embodiments, the compound is selected from the group consisting of a tetrahydroxylated bile acid, a pentahydroxylated bile acid, or a derivative thereof.

The tetra-hydroxylated bile acid may be a 3,6,7,12-tetrahydroxycholanoic acid, a 3,4,7,12-tetrahydroxycholanoic acid, a 1,3,7,12-tetrahydroxycholanoic acid, a 2,3,7,12-tetrahydroxycholanoic acid, a 3,7,16,24-tetrahydroxycholanoic acid, or a 3,7,15,24-tetrahydroxycholanoic acid, or a derivative thereof.

The 3,6,7,12-tetrahydroxycholanoic acid may be a 3α,6α,7α,12α-tetrahydroxy-5β-cholan-24-oic acid, a 3α,6β,7α,12α-tetrahydroxy-5β-cholan-24-oic acid, a 3α,6α,7β,12α-tetrahydroxy-5β-cholan-24-oic acid, a 3α,6β,7β,12α-tetrahydroxy-5β-cholan-24-oic acid, a 3α,6α,7α,12β-tetrahydroxy-5β-cholan-24-oic acid, a 3α,6β,7α,12β-tetrahydroxy-5β-cholan-24-oic acid, or a 3α,6β,7β,12β-tetrahydroxy-5β-cholan-24-oic acid, or a derivative thereof.

The 3,6,7,12-tetrahydroxycholanoic acid may be a 3β,6α,7α,12α-tetrahydroxy-5β-cholan-24-oic acid, a 3β,6β,7α,12α-tetrahydroxy-5β-cholan-24-oic acid, a 3β,6α,7β,12α-tetrahydroxy-5β-cholan-24-oic acid, a 3β,6β,7β,12α-tetrahydroxy-5β-cholan-24-oic acid, a 3β,6α,7α,12β-tetrahydroxy-5β-cholan-24-oic acid, a 3β,6β,7α,12β-tetrahydroxy-5β-cholan-24-oic acid, or a 3β,6β,7β,12β-tetrahydroxy-5β-cholan-24-oic acid, or a derivative thereof.

The 2,3,7,12-tetrahydroxycholanoic acid may be 2α,3α,7α,12α-tetrahydroxy-5β-cholanoic acid, or a derivative thereof.

The 3,4,7,12-tetrahydroxycholanoic acid may be 3α,4α,7α,12α-tetrahydroxy-5β-cholanoic acid, or a derivative thereof.

In alternative embodiments, the compound has a preferential affinity for MDR1 when compared to BSEP e.g., the compound has a high affinity for MDR1.

In alternative embodiments, the compound may be a conjugated compound, e.g., a taurine or a glycine conjugate e.g., tauryl or glycyl conjugate of a 3α,6β,7α,12β-tetrahydroxy-5β-cholan-24-oic acid, a tauryl or glycyl conjugate of a 3α,6β,7β,12β-tetrahydroxy-5β-cholan-24-oic acid, a tauryl conjugate of a 3α,6β,7α,12α-tetrahydroxy-5β-cholan-24-oic acid, or tauryl conjugate of a 3α,6β,7β,12α-tetrahydroxy-5β-cholan-24-oic acid.

In alternative embodiments, the method may comprise administering at least one other therapeutic or prophylactic agent e.g., an agent having preferential affinity for BSEP, or at least one other nutritional supplement. The therapeutic or prophylactic agent or nutritional supplement may be ursodeoxycholate or a variant or derivative thereof.

In alternative embodiments, the biliary disorder may be benign biliary strictures, benign pancreatic disease cysts, diverticulitis, liver fibrosis, liver damage, common bile duct stones, pancreatitis, pancreatic cancer or pseudocyst, periampullary cancer, bile duct carcinoma, primary sclerosing cholangitis, autoimmune cholangitis, extrinsic duct compression (e.g., compression due to a mass or tumor on a nearby organ), viral hepatitis, sepsis, bacterial abscess, use of drugs e.g., drug-induced idiosyncratic hepatotoxicity, lymphoma, tuberculosis, metastatic carcinoma, sarcoidosis, amyloidosis, intravenous feeding, primary biliary cirrhosis, primary sclerosing cholangitis, alcoholic hepatitis with or without cirrhosis, nonalcoholic steatohepatitis, nonalcoholic fatty liver disease, chronic hepatitis with or without cirrhosis, intrahepatic cholestasis of pregnancy, biliary calculosis, biliary dyscinesia, Sjogren syndrome, Wilson's disease, ischemia, toxins, alcohol, acute liver failure, α1-antitrypsin deficiency, PFIC2, Benign Recurrent Intrahepatic Cholestasis, hepatocellular carcinoma, portal hypertension, veno-occlusive disease, or hepatic vein thrombosis. The biliary disorder may arise or potentially arise from cholestasis.

In alternative embodiments, the subject may be a human.

This summary of the invention does not necessarily describe all features of the invention.

BRIEF DESCRIPTION OF THE DRAWINGS

FIG. 12 A-C shows induction of bile flow rate (BFR) by THBA in wild-type mice. (A) BFR as a function of body weight (BW) before and after the infusion of 3α,6β,7α,12α-tetrahydroxy-5β-cholan-24-oic acid 3α,6β,7α,12α-tetrahydroxy-5β-cholan-24-oic acid (6β,7α THBA) of 65 (○, open circle), 250 (*star), 350 (▲, solid triangle) and 400 (■, solid square) μmol/kg BW. (B). BFR as a function of body weight before and after the infusion of 3α,6α,7α,12α-tetrahydroxy-5β-cholan-24-oic acid (6α 7α THBA) of 65 (○, open circle) and 200 (■, solid square) μmol/kg BW. (C). BFR as a function of body weight before and after the infusion of 65 μmol/kg body weight of 6β, 7αTHBA (■, solid square), 6α, 7αTHBA (▲, solid triangle) and ursodeoxycholic acid (UDC) (0, open circle). Results are represented as the mean±the standard deviation of three mice. UDC at 65 μmol/kg body weight is the maximum tolerated dose (MTD) in the mice.

DETAILED DESCRIPTION

Figure 1:
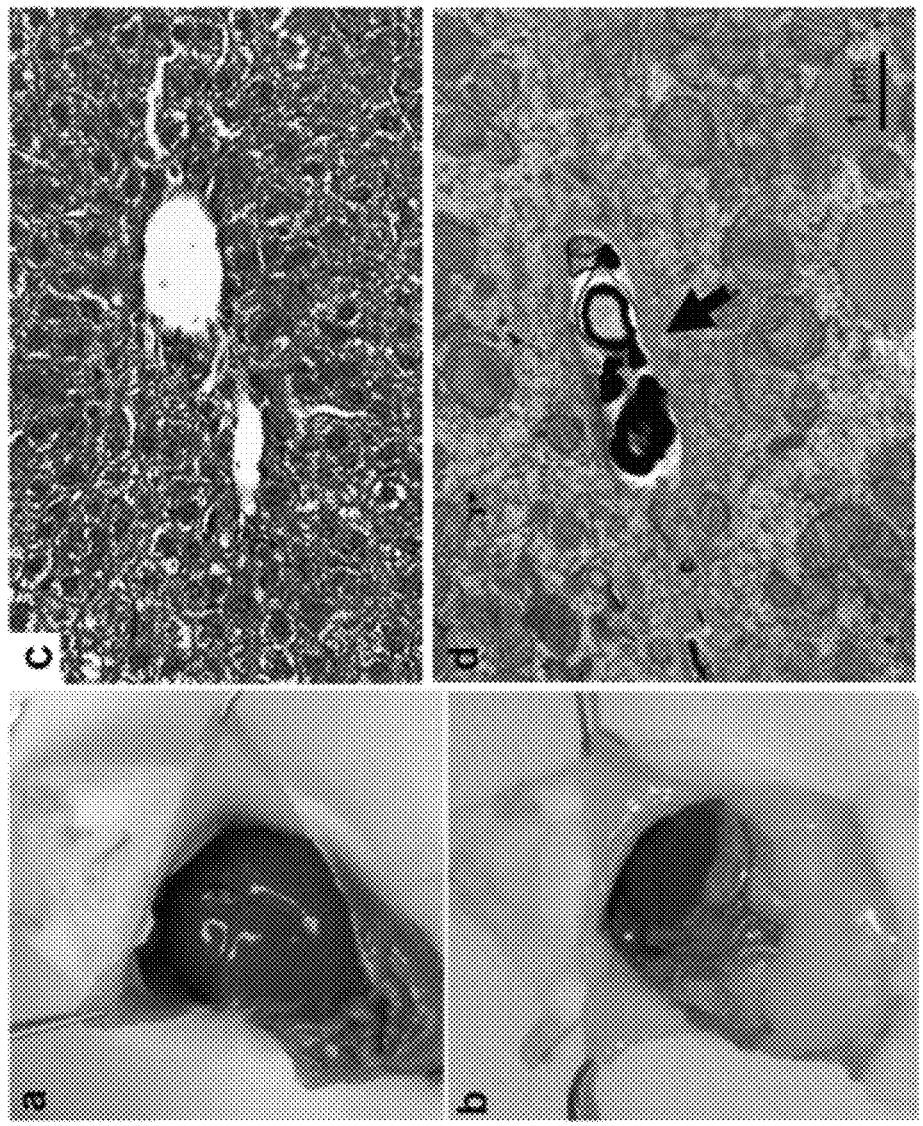
FIG. 1 shows the cholestatic phenotype of the triple knockout (bsep$^{-/-}$/mdr1a$^{-/-}$/1b$^{-/-}$) mice: a) A view of abdomens showing liver enlargement of a TKO mouse in comparison with b) a wildtype mouse; c) Periportal fibrosis in the livers of a two month old male TKO mouse (Masson trichrome staining), 40x; d) Ultrastructual changes in hepatocytes, showing dilated canalicular lumen, loss of microvilli (arrows), and retained biliary material in the form of lamellae.

The present invention provides, in part, polyhydroxylated bile acids as agents of bile salt therapy to promote or improve biliary secretion in subjects with biliary disorders. Compounds according to the invention can be used in combination with the existing compounds, such as ursodeoxycholate or a variant or derivative thereof, to improve liver function and/or ameliorate a bile disorder. The polyhydroxylated bile acids of the invention are choleretic (possess bile flow-stimulating properties) when administered to a subject e.g., a child awaiting liver transplantation. In alternative embodiments, the invention provides polyhydroxylated bile acids for stimulating bile flow in any subject, for example, a subject not diagnosed with a biliary disorder. By "stimulating bile flow" is meant increasing bile flow in a subject relative to a standard (e.g., standard levels of bile acid in an organism), or relative to the level of bile measured in the subject prior to administration of a polyhydroxylated bile acid according to the invention. The increase may be a change of any integer value between 5% and 95%, or between 10% and 90%, or between 30% and 60%, or may be over 100%. As used herein, a subject may be a human, non-human primate, rat, mouse, cow, horse, pig, sheep, goat, dog, cat, etc. The subject may be a clinical patient, a clinical trial volunteer, an experimental animal, etc. The subject may be suspected of having or at risk for having a biliary disorder, be diagnosed with a biliary disorder, or be subject confirmed to not have a biliary disorder. Diagnostic methods for biliary disorders and methods for measurement of bile flow, as well as the clinical delineation of biliary disorder diagnoses, are known to those of ordinary skill in the art.

Biliary Disorders

Biliary disorders include any disorder or condition that can be ameliorated, treated or prevented by the administration of a polyhydroxylated bile acid. Exemplary biliary disorders may include without limitation bile deficiency, bile toxicity, digestive disorders, impaired liver function, cholestasis, portal hypertension, etc.

Cholestasis refers to a condition in which the flow of bile from the liver is reduced or blocked, or in which there is a failure in bile flow. Bile flow failures may arise anywhere in the hepatic and biliary system. In general, cholestasis may be extrahepatic cholestasis, which occurs outside the liver cells, or may be intrahepatic cholestasis, which occurs inside the liver cells.

Extrahepatic cholestasis can result from benign biliary strictures, benign pancreatic disease cysts, diverticulitis, liver damage, common bile duct stones, pancreatitis, pancreatic cancer or pseudocyst, periampullary cancer, bile duct carcinoma primary sclerosing cholangitis, extrinsic duct compression, for example, compression due to a mass or tumor on a nearby organ.

Intrahepatic cholestasis can be caused by viral hepatitis including but not limited to Hepatitis B and C, sepsis, bacterial abscess, drugs e.g., drug-induced idiosyncratic hepatotoxicity, lymphoma, tuberculosis, metastatic carcinoma, sarcoidosis, amyloidosis, intravenous feeding, primary biliary cirrhosis, primary sclerosing cholangitis, alcoholic hepatitis with or without cirrhosis, chronic hepatitis with or without cirrhosis, pregnancy, Sjogren syndrome, etc. Drug-induced cholestasis is the blockage of the flow of bile from the liver caused by medication, and may be caused by: gold salts, nitrofurantoin, anabolic steroids, oral contraceptives, chlorpromazine, prochlorperazine, sulindac, cimetidine, erythromycin, tobutamide, imipramine, ampicillin and other penicillin-based antibiotics, etc. Drug-induced cholestasis and hepatotoxicity are common obstacles to drug therapy in the clinic and pose major problems for drug development and for novel applications of approved drugs. Drug-induced cholestasis also accounts for 2-5% of patients hospitalized with jaundice, ~10% of all cases of acute hepatitis, and over 50% of acute liver failure.

Cholestasis may also result from inherited cholestatic liver disease, from drug-induced cholestasis arising from the BSEP-inhibitory activity of certain drugs, and acute hepatotoxic reactions brought about by drugs and inflammatory conditions which impact liver function.

Portal hypertension refers to a disorder manifesting as increased pressure in the portal vein, which is the vein that conducts blood from the intestine to the liver. The increased pressure in the portal vein may be due to a variety of causes, including inflammation, fibrosis, splenic arteriovenous fistulae, splenic or portal vein thrombosis, massive splenomegaly, sarcoidosis, schistosomiasis, nodular regenerative hyperplasia, primary biliary cirrhosis, hepatitis, autoimmune disease, etc.

A biliary disorder according to the invention is any disorder arising, or potentially arising, from cholestasis, portal hypertension, or any disorder benefited by the administration of a poly-hydroxylated bile acid as described herein. Biliary disorders include without limitation benign biliary strictures, benign pancreatic disease cysts, diverticulitis, liver fibrosis, liver damage, common bile duct stones, pancreatitis, pancreatic cancer or pseudocyst, periampullary cancer, bile duct carcinoma, primary sclerosing cholangitis, autoimmune cholangitis, extrinsic duct compression (e.g., compression due to a mass or tumor on a nearby organ, viral hepatitis (e.g., Hepatitis A, B, C, D, E, herpes simplex, cytomegalovirus, Epstein-Barr, adenovirus), sepsis, bacterial abscess, use of drugs e.g., drug-induced idiosyncratic hepatotoxicity, lymphoma, tuberculosis, metastatic carcinoma, sarcoidosis, amyloidosis, intravenous feeding, primary biliary cirrhosis, primary sclerosing cholangitis, alcoholic hepatitis with or without cirrhosis, nonalcoholic steatohepatitis, nonalcoholic fatty liver disease, chronic hepatitis with or without cirrhosis, intrahepatic cholestasis of pregnancy, biliary calculosis, biliary dyscinesia, Sjogren syndrome, Wilson's disease, biliary disorders arising from ischemia, toxins, or alcohol, acute liver failure, α1-antitrypsin deficiency, PFIC2, Benign Recurrent Intrahepatic Cholestasis (BRIC), hepatocellular carcinoma (HCC), portal hypertension, veno-occlusive disease, hepatic vein thrombosis, etc.

Polyhydroxylated Bile Acids and Derivatives Thereof

Bile acids are amphipathic compounds derived from cholesterol and are a subclass of steroids. Bile acids and bile alcohols are steroids whose structure is related to cholane or cholestane; accordingly bile acids and bile alcohols may be termed cholanoids (51). The term "bile acid" is a generic term for cholanoid molecules having a carboxyl group and does not denote an ionization state.

The term "bile salt" may be used for a salt in which the anion is a conjugated bile acid, an unconjugated bile acid, or a conjugate of a bile alcohol, or may be used as a generic term to include both conjugated bile acids and bile alcohol conjugates occurring in nature as water-soluble anions (51). For example, bile salts may be bile acids conjugated with glycine or taurine as sodium salts.

The numbering system for the carbon atoms of the bile acid skeleton, as used herein, is as follows.

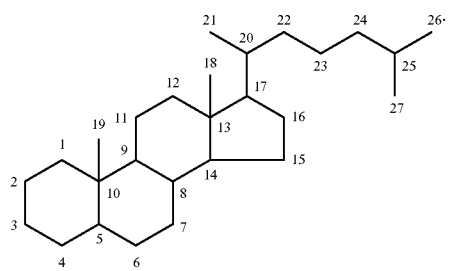

$C_{24}$ bile acids are termed cholanoic acids or cholanoates, while $C_{27}$ bile acids are termed cholestanic acids or cholestanoates. In general, the configuration of the side chain is 17β, with a 5β hydrogen (A/B ring junction in cis configuration). "Allo" bile acids are bile acids with a 5β hydrogen (51).

Bile acids may be polyhydroxylated. A polyhydroxylated bile acid compound according to the invention includes without limitation tetrahydroxylated bile acids, pentahydroxylated bile acids, hexahydroxylated bile acids, etc., up to the maximum level of hydroxylation possible.

In some embodiments, a polyhydroxylated bile acid may be a compound as represented in Formula I:

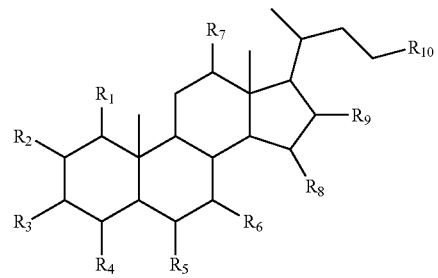

or a derivative thereof, in which any one of $R_1$ to $R_9$ may be —H or —OH, provided that at least four of $R_1$ to $R_9$ are —OH; and $R_{10}$ may be —COOH or —CH$_2$OH.

In some embodiments, any one of $R_1$ to $R_9$ may be —H, —OH, —F, —Cl, —Br, alkyl (for example, —CH$_3$, —CH$_2$—CH$_3$), —SO$_4$, or glucose provided that at least four of $R_1$ to $R_9$ are —OH; and $R_{10}$ may be —COOH or —CH$_2$OH.

In some embodiments, bile acids according to the invention are at least tetrahydroxylated i.e. have four or greater than four hydroxyl groups. In some embodiments, the hydroxyl groups are present on the steroid nucleus. In some embodiments, the hydroxyl groups may also be present on the alkyl side chain.

A tetrahydroxylated bile acid according to the invention includes, without limitation, a 3,6,7,12-tetrahydroxycholanoic acid; a 3,4,7,12-tetrahydroxycholanoic acid; a 1,2,7,12-tetrahydroxycholanoic acid; a 1,3,7,12-tetrahydroxycholanoic acid; a 2,3,7,12-tetrahydroxycholanoic acid; a 3,7,16,24-tetrahydroxycholanoic acid; or a 3,7,15,24-tetrahydroxycholanoic acid, or derivatives thereof.

A 3,6,7,12-tetrahydroxycholanoic acid according to the invention includes, without limitation, a 3α,6α,7α,12α-tetrahydroxy-5β-cholan-24-oic acid; a 3α,6β,7α,12α-tetrahydroxy-5β-cholan-24-oic acid; a 3α,6α,7β,12α-tetrahydroxy-5β-cholan-24-oic acid; a 3α,6β,7β,12α-tetrahydroxy-5β-cholan-24-oic acid; a 3α,6α,7α,12β-tetrahydroxy-5β-cholan-24-oic acid; a 3α,6β,7α,12β-tetrahydroxy-5β-cholan-24-oic acid, or a 3α,6β,7β,12β-tetrahydroxy-5β-cholan-24-oic acid, or derivatives thereof.

A 3,4,7,12-tetrahydroxycholanoic acid according to the invention includes, without limitation, a 3α,4β,7α,12α tetrahydroxy-5β-cholan-24-oic acid, a 3α,4α,7α,12α-tetrahydroxy-5β-cholanoic acid, or derivatives thereof.

A 1,3,7,12-tetrahydroxycholanoic acid according to the invention includes, without limitation, a 1β,3α,7α,12α tetrahydroxy-5β-cholan-24-oic acid, or derivatives thereof.

A 2,3,7,12-tetrahydroxycholanoic acid according to the invention includes, without limitation, a 2β,3α,7α,12α tetrahydroxy-5β-cholan-24-oic acid, a 2α,3α,7α,12α-tetrahydroxy-5β-cholanoic acid, or derivatives thereof.

A 3,7,16,24-tetrahydroxycholanoic acid according to the invention includes, without limitation, a 3α,7α,7α,16α, 24 tetrahydroxy-5β-cholane or derivatives thereof.

A 3,7,15,24-tetrahydroxycholanoic acid, according to the invention includes without limitation, a 3α,7β,15α,24 tetrahydroxy-5β-cholane or derivatives thereof.

In alternative embodiments, polyhydroxylated bile acid compounds according to the invention include, without limitation, a 3α,7α,12α,24 tetrahydroxy-5β-26-oic acid; a 3α,7α,12α,24 tetrahydroxy-5β-Cholest-25-ene; a 3α,7α,24, 26 tetrahydroxy-5β-Cholestane; or a 3α,7α,12α,24,26 pentahydroxy-5β-Cholestane or derivatives thereof.

In alternative embodiments, polyhydroxylated bile acid compounds according to the invention specifically exclude beta-muricholate and trihydroxy bile acids. In alternative embodiments, polyhydroxylated bile acid compounds according to the invention are more hydrophilic than cholate (23, 24), as measured for example by the distribution and configurations of polar [OH⁻] and apolar (H⁺) residues along the steroid ring, or by retention times in reverse-phase HPLC (60). In some embodiments, polyhydroxylated bile acid compounds according to the invention have a hydrophobicity of less than 0.45, 0.40, 0.35, 0.30, 0.25, 0.20, 0.15, 0.10, or 0.05 relative to taurocholate (which is assigned a value of 1.0; see for example Asamoto et al. (21)).

In some embodiments, polyhydroxylated bile acid compounds according to the invention have a preferential affinity for MDR1 when compared to BSEP. In some embodiments, polyhydroxylated bile acid compounds according to the invention have a high affinity to MDR1, e.g., a Km lower than 10 μM, 20 μM, 30 μM, 40 μM, 50 μM, 60 μM, 70 μM, 80 μM, 90 μM, 100 μM or more.

The term "conjugated bile acid" may be used to indicate a bile acid conjugated to a group that gives additional hydrophilicity or charge to the molecule. In alternative embodiments, the polyhydroxylated bile acid compounds according to the invention include taurine and/or glycine conjugates. In alternative embodiments, the polyhydroxylated bile acid compounds according to the invention include conjugates with any other suitable amino acids. In alternative embodiments, the polyhydroxylated bile acid compounds according to the invention include conjugates with sulfate, phosphate, Coenzyme A, glucuronate, glucose, xylose, and other sugars, N-acetylglucosamine, etc. For example, conjugated polyhydroxylated compounds according to the invention include, without limitation, tauryl or glycyl conjugates of 3α,6β,7α, 12β-tetrahydroxy-5β-cholan-24-oic acids, tauryl or glycyl conjugates of 3α,6β,7β,12β-tetrahydroxy-5β-cholan-24-oic acids, tauryl conjugates of 3α,6β,7α,12α-tetrahydroxy-5β-cholan-24-oic acids, tauryl conjugates of 3α,6β,7β,12α-tetrahydroxy-5β-cholan-24-oic acids, ethanesulfonic acid, 2-[(3,6,7,12-tetrahydroxy-24-oxocholan-24-yl)amino], e.g., ethanesulfonic acid, 2-[[(3α,5β,6α,7α,12α)-3,6,7,12-tetrahydroxy-24-oxocholan-24-yl]amino]-, Glycine, N-(3,6,7, 12-tetrahydroxy-24-oxocholan-24-yl) e.g., Glycine, N-[(3α, 5β,6β,7β,12α)-3,6,7,12-tetrahydroxy-24-oxocholan-24-yl], Glycine, N-[(3α,5β,6β,7α,12α)-3,6,7,12-tetrahydroxy-24-oxocholan-24-yl], Glycine, N-[(3α,5β,6α,7β,12α)-3,6,7,12-tetrahydroxy-24-oxocholan-24-yl], Glycine, N-[(3α,5β,6α, 7α,12α)-3,6,7,12-tetrahydroxy-24-oxocholan-24-yl], etc.

The polyhydroxylated bile acid compounds according to the invention include isomers e.g., stereoisomers. For example, 3β and 5α hydroxy tetrahydroxycholanoic acid are included, as are any stereoisomeric configurations and combinations thereof.

The polyhydroxylated bile acid compounds according to the invention include physiologically or pharmaceutically-acceptable derivatives, such as salts, esters, enol ethers, enol esters, solvates, hydrates and prodrugs of the compounds described herein. Pharmaceutically-acceptable salts, include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc, aluminum, and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

Compounds and salts thereof of this invention and for use in this invention are generally provided in substantially purified form. A compound or salt (if naturally occurring) is "substantially pure" or "isolated" when it is separated from the components that naturally accompany it (e.g, cells of a source organism or tissue). A compound may be substantially pure or isolated when it is substantially free of cellular contaminants, i.e, that it is present ex vivo and in a concentration greater than that of the compound in a source organism, tissue, or other natural source. Typically, a compound is substantially pure or isolated when it is at least 10%, 20%, 30%, 40%, 50%, or 60%, more generally 70%, 75%, 80%, or 85%, or over 90%, 95%, or 99% by weight, of the total material in a sample. Thus, for example, a compound that is chemically synthesized will generally be substantially free from its naturally associated components. A substantially pure compound can be obtained, for example, by extraction from a natural source or by chemical synthesis. A substantially pure compound may include stereoisomers or differentially hydroxylated mixtures. Purity can be measured using any appropriate method such as column, gas, or liquid chromatography or mass spectrometry.

In an alternative embodiment of the invention, a composition comprising a racemic mixture of a tetrahydroxylated bile acid is provided. The racemic mixture may be produced as a result of the chemical synthesis of the tetrahydroxylated bile acid; alternatively, two or more stereochemically pure enantiomers may be combined. In another embodiment, the composition may comprise two or more tetrahydroxylated bile acids.

Preparation of Polyhydroxylated Bile Acids

Compounds according to the invention, or for use according to the invention, including pharmaceutically acceptable salts or derivatives thereof, may be obtained by synthesis making use of common procedures as exemplified herein or known in the art. Some compounds that may be used according to the invention can be obtained from natural sources. For example, polyhydroxylated bile acid compounds may be prepared in part or in whole from natural sources, e.g., by fractionating biological extracts (e.g, from bsep KO mice). Bile acids may be obtained from bsep KO mice by for example using bile duct cannulation to collect about 10-20 ml bile from 50-100 bsep KO mice. HPLC may be used to isolate about 10-20 μmol (5-10 mg) tetra-hydroxylated bile acid. In some embodiments, polyhydroxylated bile acid compounds according to the invention may be prepared by total synthesis. Such synthetic compounds can, optionally, be labeled or derivatized for analytical or drug development purposes.

The compounds may be synthesized using standard techniques such as those described in Tohma et al., 1985 (52); Iida et al., 1991a (53); Iida et al., 1991b (54); Aggarwal et al., 1992 (55); Iida et al., 1993 (56); Kurosawa et al., 1995 (57); Kurosawa et al., 1996 (58); Iida et al, 2002 (59); Tserng K Y and Klein P D (1977), Leppik R A (1983), or Iida T. et al. (1990) etc., all of which are specifically incorporated by reference. For example, tetrahydroxy bile acids may be prepared as indicated in Tohma et al., 1985 (52); Iida et al., 1991b (54); Aggarwal et al., 1992 (55); Iida et al., 1993 (56); Kurosawa et al., 1996 (58); Iida et al, 2002 (59); pentahydroxy bile acids may be prepared as indicated in Kurosawa et al., 1996 (58).

Pharmaceutical or Nutritional Supplement Compositions, Dosages, and Administration of Poly-Hydroxylated Bile Acids The polyhydroxylated bile acid compounds of the invention can be provided alone or in combination with other compounds (for example, nucleic acid molecules, small molecules, peptides, or peptide analogues), in the presence of a liposome, an adjuvant, or any pharmaceutically or physiologically acceptable carrier, in a form suitable for administration to humans or animals. If desired, treatment with a compound according to the invention may be combined with more traditional and existing therapies for biliary disorders or disorders resulting in or potentially resulting in hepatotoxicity, or with existing nutritional supplements for stimulating bile flow. In some embodiments, polyhydroxylated bile acids according to the invention are administered to subjects not diagnosed with a biliary disorder (e.g., a normal subject) to stimulate bile flow. In some embodiments, polyhydroxylated bile acids according to the invention are administered under conditions where BSEP is inhibited and where the approved therapeutic agent for cholestasis, ursodeoxycholate, is ineffective. In some embodiments, polyhydroxylated bile acids according to the invention are administered together with ursodeoxycholate or a variant or derivative thereof (e.g., sulfated ursodeoxycholate, nitrodeoxycholate, taurodeoxycholate, etc.), Rifampicin, or any compound useful for treating cholestasis or portal hypertension or for stimulating bile flow.

Conventional pharmaceutical or nutritional supplement formulation practice may be employed to provide suitable formulations or compositions to administer the compounds to patients suffering from or presymptomatic for cholestasis, or to normal subjects for stimulating bile flow. Any appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences" (19th edition), ed. A. Gennaro, 1995, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

For therapeutic or prophylactic compositions, the compounds are administered to a subject in an amount sufficient to stop or slow cholestasis or to maintain or increase bile flow or to ameliorate portal hypertension. For nutritional supplements, the compounds are administered to a subject in an amount sufficient to stimulate bile flow.

As discussed herein, a significant upregulation of MDR1 expression was found in livers of PFIC patients, indicating that MDR1 can be targeted in drug therapy for cholestatic diseases such as PFIC2 and other biliary disorders indicated herein. BSEP and MDR1 are loci of significant polymorphism in human populations, and some BSEP variants are associated with susceptibility to liver diseases. For example, the V444A polymorphism in BSEP is present in about half the population and is associated with a ~60% increased risk of intrahepatic cholestasis of pregnancy. Other forms of biliary disorders manifesting elevated MDR1 expression can also be treated using the compounds according to the invention. Compounds according to the invention can also provide therapeutic benefit to patients suffering from inherited cholestatic liver disease, from drug-induced cholestasis arising from the BSEP-inhibitory activity of certain drugs, or from other biliary disorders, and can help alleviate acute hepatotoxic reactions brought about by drugs and inflammatory conditions which impact biliary function.

An "effective amount" of a compound according to the invention includes a therapeutically effective amount or a prophylactically effective amount or a nutritionally effective amount. A "therapeutically effective amount" refers to an amount effective, at dosages and for periods of time necessary, to achieve the desired therapeutic result, such as increased bile flow, relief of jaundice, or improved liver functions as indicated by normalization of serum liver biochemical indicators, such as the levels of bilirubins, ALP (alkaline phosphatase), ALT (alanine aminotransferase), AST (aspartate aminotransferase), γ-GT (Gamma-Glutamyl Transpeptidase), etc. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as increased bile flow or improved liver functions as indicated by liver biochemical indicators, increased bile flow, relief of jaundice, or improved liver functions as indicated by normalization of serum liver biochemical indicators, such as the levels of bilirubins, ALP (alkaline phosphatase), ALT (alanine aminotransferase), AST (aspartate aminotransferase), γ-GT (Gamma-Glutamyl Transpeptidase), etc. Typically, a prophylactic dose is used in subjects prior to or at an earlier stage of disease, so that a prophylactically effective amount may be less than a therapeutically effective amount. An exemplary range for therapeutically or prophylactically effective amounts of a compound may be 5-50 mg/day/kg of body weight of the subject e.g., a human. A "nutritionally effective amount" refers to an amount effective, at dosages and for periods of time necessary, to achieve the desired result, such as increased bile flow or improved liver functions as indicated by liver biochemical indicators.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In the case of vaccine formulations, an immunogenically effective amount of a compound of the invention can be provided, alone or in combination with other compounds, with an adjuvant, for example, Freund's incomplete adjuvant or aluminum hydroxide. The compound may also be linked with a carrier molecule, such as bovine serum albumin or keyhole limpet hemocyanin to enhance immunogenicity.

For nutritional supplements, at least one additive, including one listed below, can be included for consumption with the nutritional supplement of the invention and may have, for example, antioxidant, dispersant, antimicrobial, or solubilizing properties. A suitable antioxidant is, for example, vitamin C, vitamin E or rosemary extract. A suitable dispersant is, for example, lecithin, an alkyl polyglycoside, polysorbate 80 or sodium lauryl sulfate. A suitable antimicrobial is, for example, sodium sulfite or sodium benzoate. A suitable solubilizing agent is, for example, a vegetable oil such as sunflower oil, coconut oil, and the like, or mono-, di- or triglycerides. Additives include vitamins such as vitamin A (retinol, retinyl palmitate or retinol acetate), vitamin B1 (thiamin, thiamin hydrochloride or thiamin mononitrate), vitamin B2 (riboflavin), vitamin B3 (niacin, nicotinic acid or niacinamide), vitamin B5 (pantothenic acid, calcium pantothenate, d-panthenol or d-calcium pantothenate), vitamin B6 (pyridoxine, pyridoxal, pyridoxamine or pyridoxine hydrochloride), vitamin B12 (cobalamin or cyanocobalamin), folic acid, folate, folacin, vitamin H (biotin), vitamin C (ascorbic acid, sodium ascorbate, calcium ascorbate or ascorbyl palmitate), vitamin D (cholecalciferol, calciferol or ergocalciferol), vitamin E (d-alpha-tocopherol, d-beta-tocopherol, d-gamma-tocopherol, d-delta-tocopherol or d-alpha-tocopheryl acetate) and vitamin K (phylloquinone or phytonadione). Other additives include minerals such as boron (sodium tetraborate decahydrate), calcium (calcium carbonate, calcium caseinate, calcium citrate, calcium gluconate, calcium lactate, calcium phosphate, dibasic calcium phosphate or tribasic calcium phosphate), chromium (GTF chromium from yeast, chromium acetate, chromium chloride, chromium trichloride and chromium picolinate) copper (copper gluconate or copper sulfate), fluorine (fluoride and calcium fluoride), iodine (potassium iodide), iron (ferrous fumarate, ferrous gluconate or ferrous sulfate), magnesium (magnesium carbonate, magnesium gluconate, magnesium hydroxide or magnesium oxide), manganese (manganese gluconate and manganese sulfate), molybdenum (sodium molybdate), phosphorus (dibasic calcium phosphate, sodium phosphate), potassium (potassium aspartate, potassium citrate, potassium chloride or potassium gluconate), selenium (sodium selenite or selenium from yeast), silicon (sodium metasilicate), sodium (sodium chloride), strontium, vanadium (vanadium sulfate) and zinc (zinc acetate, zinc citrate, zinc gluconate or zinc sulfate). Other additives include amino acids, peptides, and related molecules such as alanine, arginine, asparagine, aspartic acid, carnitine, citrulline, cysteine, cystine, dimethylglycine, gamma-aminobutyric acid, glutamic acid, glutamine, glutathione, glycine, histidine, isoleucine, leucine, lysine, methionine, ornithine, phenylalanine, proline, serine, taurine, threonine, tryptophan, tyrosine and valine. Other additives include animal extracts such as cod liver oil, marine lipids, shark cartilage, oyster shell, bee pollen and d-glucosamine sulfate. Other additives include unsaturated free fatty acids such as linoleic, arachidonic and linolenic acid, which may be in an ester (e.g. ethyl ester or triglyceride) form. Other additives include herbs and plant extracts such as kelp, pectin, Spirulina, fiber, lecithin, wheat germ oil, safflower seed oil, flax seed, evening primrose, borage oil, blackcurrant, pumpkin seed oil, grape extract, grape seed extract, bark extract, pine bark extract, French maritime pine bark extract, muira puama extract, fennel seed extract, dong quai extract, chaste tree berry extract, alfalfa, saw palmetto berry extract, green tea extracts, angelica, catnip, cayenne, comfrey, garlic, ginger, ginseng, goldenseal, juniper berries, licorice, olive oil, parsley, peppermint, rosemary extract, valerian, white willow, yellow dock and yerba mate. Other additives include enzymes such as amylase, protease, lipase and papain as well as miscellaneous substances such as menaquinone, choline (choline bitartrate), inositol, carotenoids (beta-carotene, alpha-carotene, zeaxanthin, cryptoxanthin or lutein), para-aminobenzoic acid, betaine HCl, free omega-3 fatty acids and their esters, thiotic acid (alpha-lipoic acid), 1,2-dithiolane-3-pentanoic acid, 1,2-dithiolane-3-valeric acid, alkyl polyglycosides, polysorbate 80, sodium lauryl sulfate, flavanoids, flavanones, flavones, flavonols, isoflavones, proanthocyanidins, oligomeric proanthocyanidins, vitamin A aldehyde, a mixture of the components of vitamin $A_2$, the D Vitamins ($D_1$, $D_2$, $D_3$ and $D_4$) which can be treated as a mixture, ascorbyl palmitate and vitamin $K_2$. The nutritional supplement of the invention is typically a viscous oil and can be added to a foodstuff composition during processing of the foodstuff. Such a foodstuff composition is often referred to as a functional food, and can be any food that will tolerate the physicochemical properties of the nutritional supplement, for example, margarine, cooking oil, shortening or mayonnaise. It can also be packaged for consumption in softgel, capsule, tablet or liquid form. It can be supplied in edible polysaccharide gums, for example carrageenan, locust bean gum, guar, tragacanth, cellulose and carboxymethylcellulose.

In general, compounds of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the ED50 (the minimum dose effective for 50% of the population). Other methods that may be used to determine toxicity of the compounds of the invention include, but are not limited to, histological abnormality by H&E staining, trichrome staining or the like; changes in bile flow rate, and/or clearance of other bile substances (for example, as determined by bile duct cannulation); HPLC analysis, enzymatic assays or the like; changes in liver indicator profiles, for example level of bilirubins, level of ALP (alkaline phosphatase), level of ALT (alanine aminotransferase), level of AST (aspartate aminotransferase), level of γ-GT (Gamma-Glutamyl Transpeptidase), or the like. The maximum tolerated dose (MTD) is the highest regularly administered dose of a compound or composition that does not cause overt toxicity (e.g. does not cause unacceptable side effects) in a subject study over a period of time. The subject may be a human, or an animal, such as a mouse or a rat, for example. The regularly administered dose may be a daily dose, administered as a single bolus; alternately the daily dose may be divided into two or more partial doses so that the subject receives the total daily dose over time. The period of time of the study may vary from a few days to a few months, for example 10, 20, 30, 60, 90 or 120 days, or any amount therebetween. Examples of overt toxicity may include, but are not limited to, appreciable death of cells or organ dysfunction, toxic manifestations that are predicted materially to reduce the life span of the subject, or 10% or greater retardation of body weight gain.

In some circumstances however, such as in severe disease conditions, it may be necessary to administer substantial excesses of the compositions. In some embodiments, 3α,6α,7α,12α-tetrahydroxy-5β-cholan-24-oic acid or 3α,6β,7α,12α-tetrahydroxy-5β-cholan-24-oic acid may have lower toxicity than other bile acids, for example ursodexoxycholate. When used as a nutritional supplement, the appropriate dose should not result in significant toxicity.

Articles of Manufacture

Articles of manufacture containing packaging material, a polyhydroxylated bile acid compound or composition, or pharmaceutically or physiologically acceptable derivative thereof, provided herein, which is effective for stimulating bile flow or for modulating the activity of MDR1, or for treatment, prevention or amelioration of one or more symptoms of cholestasis or biliary disorders in which MDR1 is implicated, within the packaging material, and a label that indicates that the compound or composition, or pharmaceutically acceptable derivative thereof, is used for stimulating bile flow or for modulating the activity of MDR1, or for treatment, prevention or amelioration of one or more symptoms of cholestasis or biliary disorders in which MDR1 is implicated, are provided.

Kits

A kit comprising a polyhydroxylated bile acid compound, or composition comprising a polyhydroxylated bile acid compound, or pharmaceutically or physiologically acceptable derivatives thereof, provided herein, which is effective for stimulating bile flow or for modulating the activity of MDR1, or for treatment, prevention or amelioration of one or more symptoms of cholestasis or biliary disorders in which MDR1 is implicated, along with instructions for use of the compound or composition, is provided. The kit may be useful for treating a biliary disorder in a subject, and the instructions may include, for example, dose concentrations, dose intervals, preferred administration methods or the like.

In another embodiment, the kit may be useful for the preparation of a medicament, and the instructions may comprise instructions for the preparation of the medicament. The kit may further comprise instructions for use of the medicament in treatment for treatment, prevention or amelioration of one or more symptoms of cholestasis or biliary disorders in which MDR1 is implicated, and include, for example, dose concentrations, dose intervals, preferred administration methods or the like.

In another embodiment, the kit may be useful for the preparation of a pharmaceutical or nutritional composition, and the instructions may comprise instructions for the preparation of the pharmaceutical or nutritional composition. The kit may further comprise instructions for use of the pharmaceutical or nutritional composition for treatment, prevention or amelioration of one or more symptoms of cholestasis or biliary disorders in which MDR1 is implicated, and include, for example, dose concentrations, dose intervals, preferred administration methods or the like.

The present invention will be further illustrated in the following examples.

EXAMPLE 1

Animal Model for Cholestasis

Methods
Animals

As described previously, the bsep KO mice on an FVB/NJ genetic background (16) were maintained in this laboratory and mdr1a/1b KO mice (22) were from Taconic (Hudson, N.Y. 12534). Mice were maintained in a 12-hour light and dark cycle, at 22° C., with free access to food and water. The mice were fed a normal diet except where specified otherwise in the results. Experiments were performed using approved protocols of the Committee on Animal Care, University of British Columbia, according to the guidelines of the Canadian Council on Animal Care.

Light and Transmission Electron Microscopy

For light microscopy, mice were killed with $CO_2$ after 2-4 hours of fasting. Livers were immediately removed and transferred into 10% neutral buffered formalin followed by paraffin sectioning and hematoxylin-eosin staining or Masson trichrome staining (Wax-it Histology Services Inc, Vancouver). For transmission electron microscopy, livers were perfusion-fixed in-situ using ice-cold 2.5% glutaraldehyde and kept in 2.5% glutaraldehyde. Dehydration, plastic-embedding and sectioning were performed as described previously (25). One micron-thick plastic-embedded sections were also obtained and examined in a Philips EM400T transmission electron microscope (Eindhoven, The Netherlands).

Human Liver Samples

Five needle biopsy or surgical biopsy liver samples from genetically confirmed PFIC type 1 and 2 patients[1] aged 5 months to 1.5 years of age were obtained. Two PFIC-2 patients were sibling pairs with a heterozygous V284L mutation and a 1 bp deletion at nucleotide position 1273. The other PFIC-2 patient had a G1004D missense mutation. Three PFIC-3 patients were included by virtue of having high γ-GT PFIC, including one confirmed deletion mutation in the MDR3 gene (73). Another 6 age-matched controls (0.5 to 1.5 years) from non-jaundiced, non-cholestatic metabolic liver disease or hepatitis patients. Samples were collected under informed consent.

Quantitative Reverse-Transcription PCR

Liver samples from mice and patients were used to prepare RNA as previously described (16). Briefly, total RNAs were extracted from frozen liver by the RNAeasy kit (Qiagen GmbH, Hilden, Germany). 1-10 μg of total RNA was reverse-transcribed with 200 μmol of random hexamer (Promega Corp., Madison, Wis.) and reverse transcriptase (SuperScript H, Invitrogen Life Technologies, Breda, Netherlands) at 42° C. for 50 min and inactivated at 72° C. for 15 min. With the complementary DNA (cDNA) obtained, for mouse samples, PCR reactions were done with the SYBR Green PCRMaster Mix (Foster City, Calif.) in a PRISM 7900HT Sequence Detection System (Applied Biosystems, Foster City, Calif.), using the "Standard Curve Method" (ABI PRISM User Bulletin 2). Primers used were as reported previously (16). For each sample, aliquots (5-10 ng) of total RNA were used for each RT-PCR reaction, and the results were normalized against the expression level of ribosomal protein S15 (Rps15). For patient samples, PCR reactions were performed using the Taqman system. Aliquots (5 ng) of total RNA were used for each RT-PCR reaction. The expression levels of MDR relative to TATA box-binding protein (TBP) were calculated using the dCT method (ABI PRISM User Bulletin 2). The primers and probes used were: MDR (Hs00184500_m1, ABI) and TBP (sense: 5'-CACGAACCACGGCACTGTT-3' (SEQ ID NO: 1); antisense: 5'-TTTTCTTGCTGC-CAGTCTGGAC-3' (SEQ ID NO: 2); probe 5'-JOE TGTG-CACAGGAGCCAAGAGTGAAGA-3' (SEQ ID NO: 3)).

Immunofluorescent Staining

Samples of fresh liver tissue were embedded in O.C.T. compound (Tissue-Tek; SAKURA) immediately. Frozen tissue sections (~5-7 µm) were cut with a cryostat and placed on poly-L-lysine-coated glass slides, then fixed in cooled acetone for 10 minutes. A rabbit polyclonal antibody against human BSEP (1:500) was used as previously reported (26). Monoclonal antibodies against human MDR with 1:500 dilution (Sigma, Saint Louis Mo.) were used. After rinsing with PBS, the tissue sections were incubated with fluorescent-conjugated secondary antibody to either rabbit or mouse IgG (Alexa Fluor 594 and Alexa Fluor 488, Life Technologies) for 1 hour at room temperature, followed by PBS washing. The sections were mounted with VectaShield (Life Technologies). Images were obtained using a Nikon C1 confocal microscope and processed using Photoimpact 8.0 software (Ulead).

Results

Figure 3:
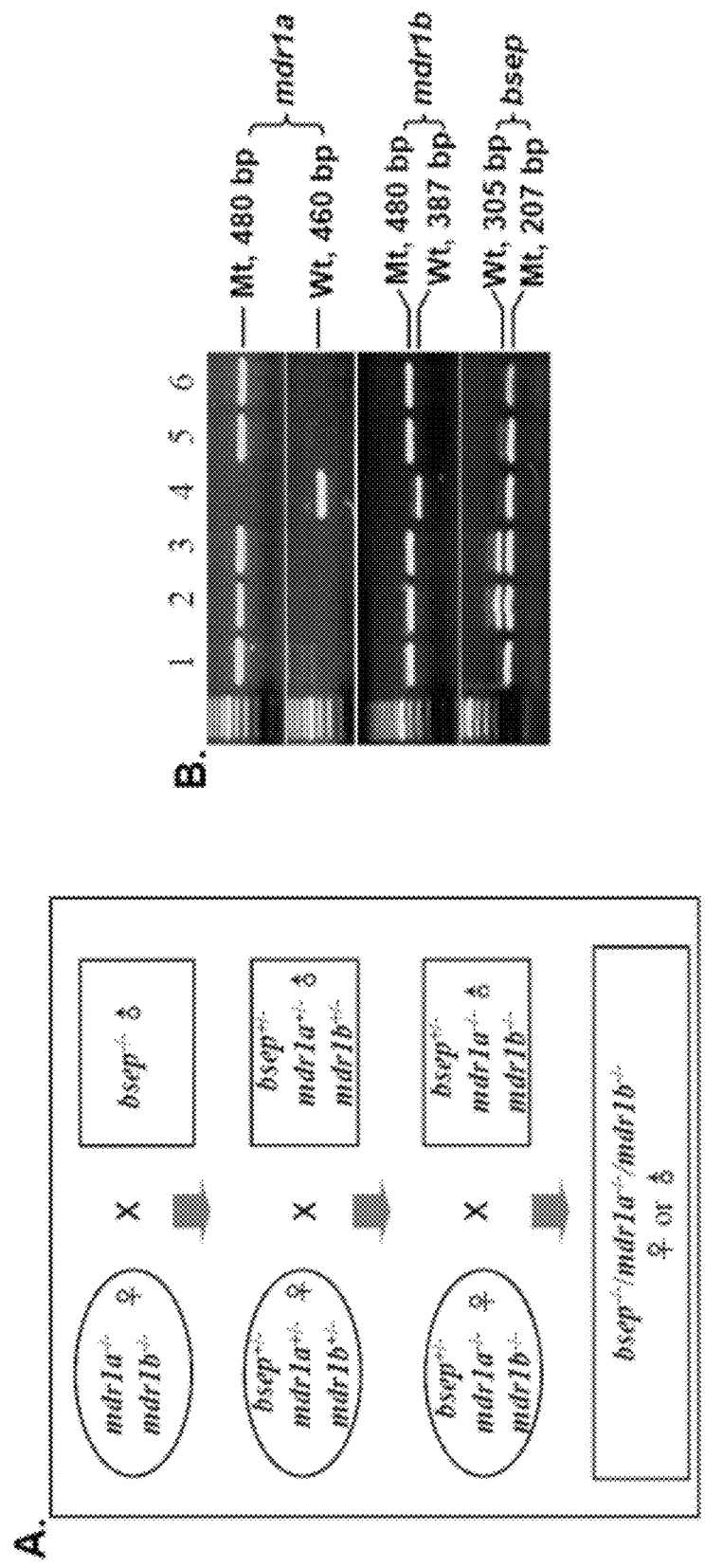
FIG. 3 shows the generation of "triple knockout" (bsep$^{-/-}$/mdr1a$^{-/-}$/mdr1b$^{-/-}$) mice: a) Crossing scheme for generating TKO mice. The mdr1a$^{-/-}$/mdr1b$^{-/-}$ double knockout and bsep$^{-/-}$ mice were used to generate the triply heterozygotic bsep$^{+/-}$/mdr1a$^{+/-}$/mdr1b$^{+/-}$ mice (100% of offspring are triple heterozygotes). The triple heterozygotes were used to produce bsep$^{+/-}$/mdr1a$^{-/-}$/mdr1b$^{-/-}$ mice (approximately ⅛ of the offspring since the mdr1a and mdr1b genes in mice are closely linked), which were then used to generate the TKO homozygotes (bsep$^{-/-}$/mdr1a$^{-/-}$/mdr1b$^{-/-}$). b) A PCR screening result for the TKO mice. Lanes 1, 5 and 6 are triple knockout mice, in which only bands from mutant alleles were amplified.

Triple knockout (TKO) mice carrying null mutations of mdr1a and mdr1b (co-orthologs of human MDR1) and bsep genes by multi-step crossing of bsep$^{-/-}$ mice (18) with mdr1a$^{-/-}$/mdr1b$^{-/-}$ double knockout mice (22) were generated FIG. 3a). Null expression of the three mutant genes in the TKO mice was confirmed by genomic PCR (FIG. 3b), real time RT-PCR (FIG. 5), and Western blotting.

Figure 2:
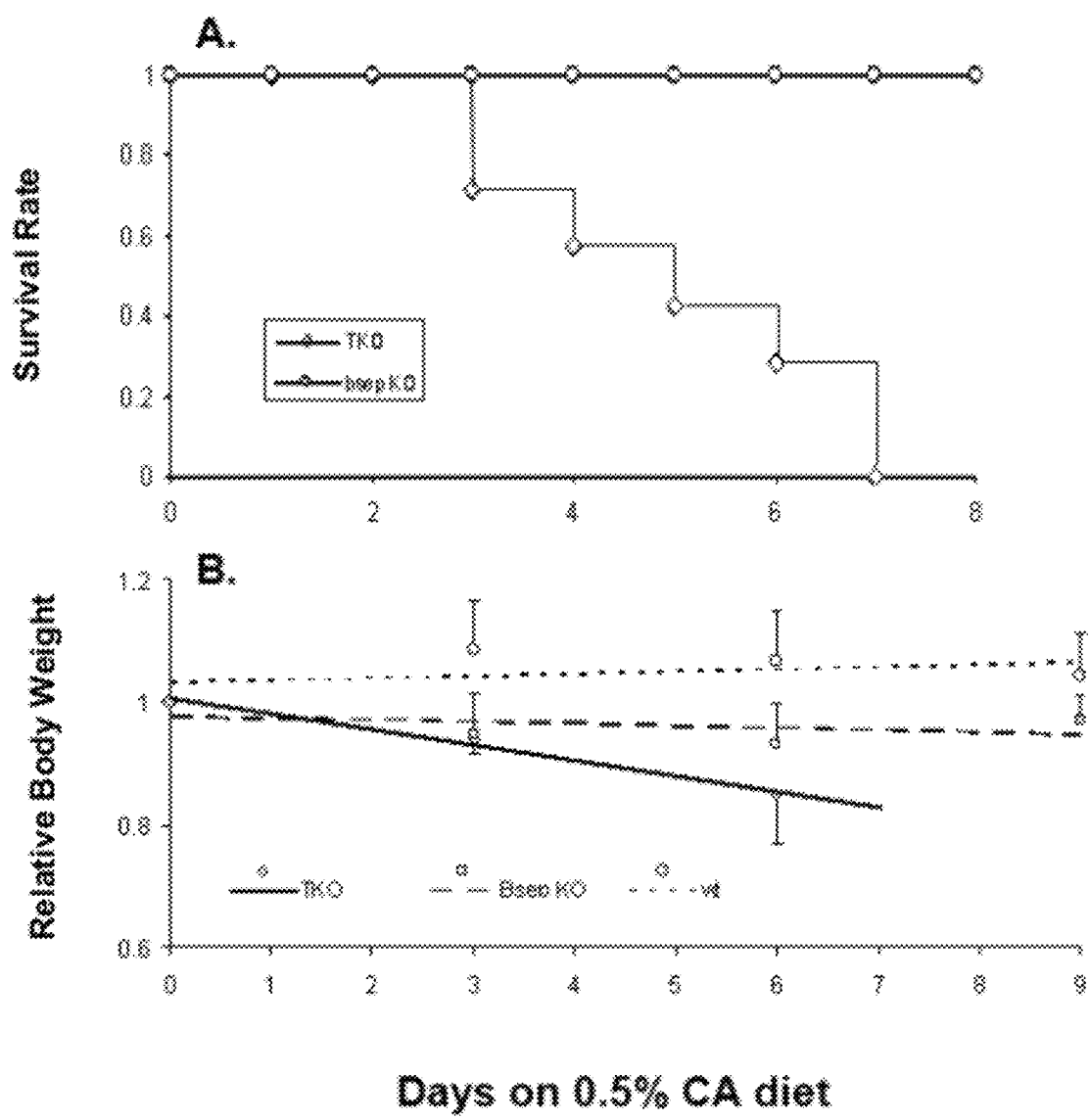
FIG. 2 shows the survival rate (a) and body weight changes (b) of the "triple knockout" (bsep$^{-/-}$/mdr1a$^{-/-}$/1b$^{-/-}$) mice after being fed 0.5% cholic acid (CA).

The TKO mice displayed more severe cholestasis than either parental strain, manifesting as severe jaundice e.g., on the body wall and paws, throughout life, liver enlargement (FIG. 1a), disrupted canaliculi (FIG. 1d), blocked bile ducts, growth retardation and very high mortality. Under close care, some TKO mice, mostly females, do live to adulthood while about 80% of the TKO males suffer sudden death within 2-6 months. The male adults are fertile and can be used for producing TKO offspring. We further demonstrated that the TKO mice have a reduced tolerance for cholestatic stress by feeding female TKO mice a 0.5% cholic acid diet, a condition that can be well-tolerated by bsep$^{-/-}$ females and mdr1a$^{-/-}$/1b$^{-/-}$ double KO mice. The female TKO mice under a 0.5% CA diet became terminally ill or died after 3-7 days of feeding (FIG. 2). This is in sharp contrast with the bsep$^{-/-}$ mice, the females of which could sustain 105 days of the same feeding conditions without showing any terminal illness (16).

Figure 4:
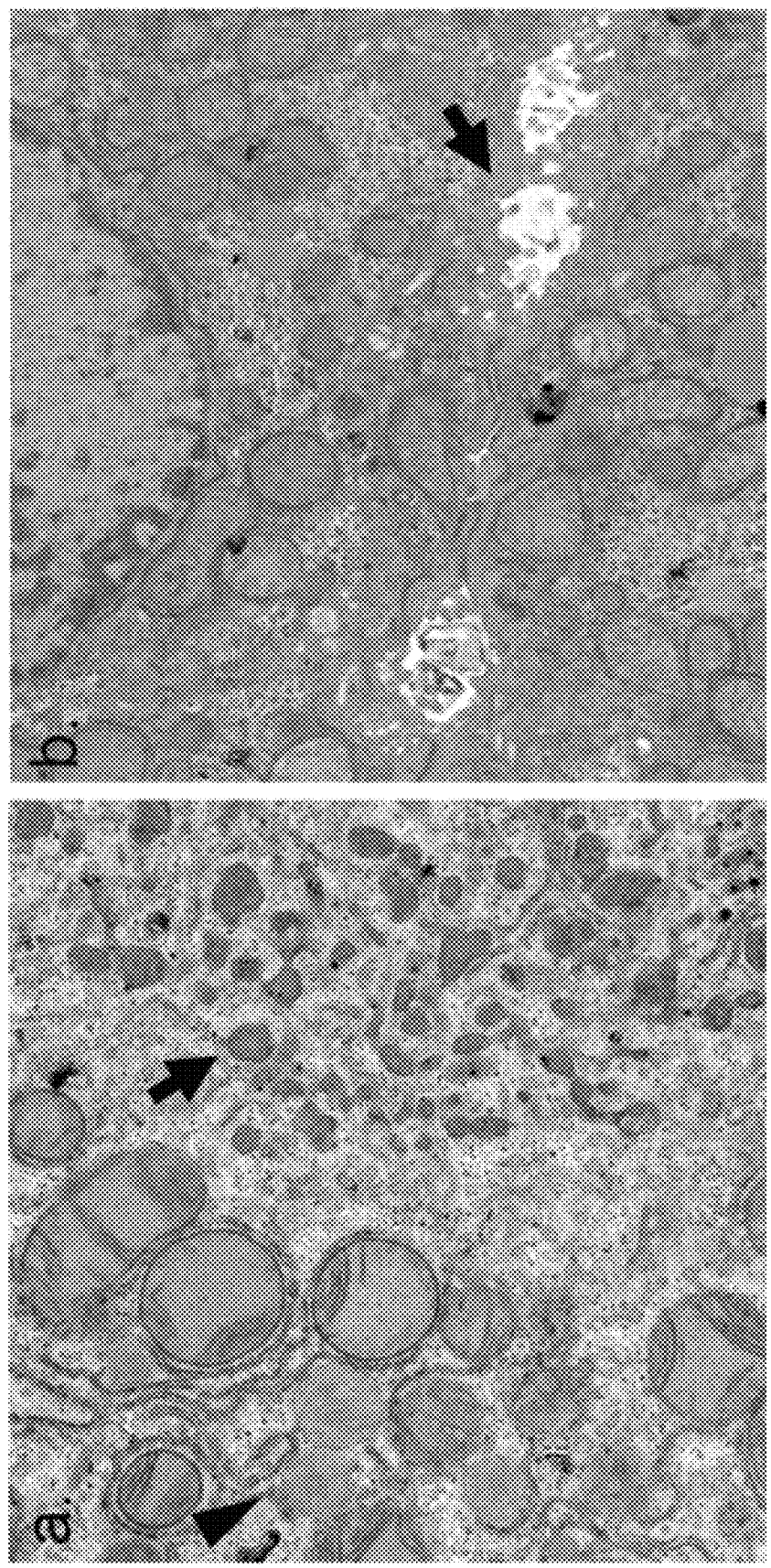
FIG. 4 shows the ultrastructual changes in hepatocytes of a TKO (bsep$^{-/-}$/mdr1a$^{-/-}$/1b$^{-/-}$) mouse and an mdr1a$^{-/-}$/1b$^{-/-}$ control that shows no ultrastructural liver abnormality. a) On the left, showing abnormal mitochondria of variable size with cristae that are pushed to one side with small ledges not crossing the midline. Their mitochondrial matrix is homogeneous and granules are absent. To the right, this image shows great numbers of hypertrophied Golgi vesicles filled with dense material (arrow). b) The liver of an mdr1a$^{-/-}$/1b$^{-/-}$ mouse showing no ultrastructural abnormalities. The arrow points to a normal canaliculus.

The histological presentation of the TKO mice also indicates a much more severe cholestasis in TKO mice than in bsep$^{-/-}$ mice. Under a microscope, the hepatocytes of TKO mice show readily visible periportal fibrosis (FIG. 1c) and paucity of bile ducts (17 bile ducts per 91 portal veins in TKO mice vs. 68 per 165 counted in wild-type mice). Using electron microscopy, profound hepatic damage was further observed in both plasma membrane and cytoplasm (FIG. 1d). The TKO mice exhibited more severe defects as manifested by severely impaired canalicului that have lost almost all microvilli, and dilated canalicular spaces filled with dense bile substances. The hepatocytes of TKO mice also display cytoplasmic abnormalities typical of hepatic toxicity with distorted mitochondria, hypertrophied Golgi apparatus, increased smooth endoplasmic reticulum, excessive lipid droplets, and increased numbers of peroxisomes (FIG. 4).

To determine whether or not Mdr1 is also a physiologically relevant canalicular bile salt transporter that helps to alleviate an otherwise more severe cholestatic phenotype, we selectively blocked Mdr1 (P-glycoprotein) with the P-glycoprotein blocker Cyclosporine A (CsA) in bsep$^{-/-}$ mice, in which the major canalicular bile salt transporter Bsep is inactivated. Peritoneal injection of 25 mg/kg/day CsA induced a more severe cholestatic phenotype, including jaundice, rapid weight loss and a typically cholestatic liver biochemical profile of liver indicators similar to PFIC2 (Table 1). This observation of CsA-induced cholestasis in bsep$^{-/-}$ knockout (KO) mice indicates that Mdr1 is indeed a physiologically relevant bile salt transporter. However, the possibility remained that the cholestatic effects of CsA on bsep$^{-/-}$ mice are due to nonspecific toxicity of the compound rather than specific inhibition of Mdr1 mediated bile salt transport. CSA-treated wild-type mice were not noticeably affected by the treatment.

The serum biochemical profile for liver function of the TKO mice resembles PFIC2, and differs from that of bsep$^{-/-}$ mice in which no such abnormalities were seen (18). Examination of the plasma liver indicator profile of TKO mice showed low γ-GT, about 2-fold higher alkaline phosphatase (Table 1) and severe cholestasis comparable to the presentation of human PFIC2. The TKO mice had serum bilirubin levels on average about 13 times that of the wildtype controls. The changes in ALT and AST were relatively small, which again agrees with what is found in PFIC2 patients (27, 28), who usually have very poor biliary secretion of bile salt with high alkaline phosphatase and bilirubin, and low or normal γ-GT in serum. The TKO mice therefore are a good model for the physiological consequences of completely abolished bile salt secretion such as that found in human PFIC2.

TABLE 1

Liver biochemical indicators in bsep$^{-/-}$, and wildtype female mice treated with Cyclosporine A for two weeks, bsep$^{-/-}$ mdr1a/b$^{-/-}$ Triple Knockout mice, bsep$^{-/-}$, mdr1a/b$^{-/-}$, and wildtype female mice fed a normal diet or fed a 0.5% CA-supplemented diet (n = 4)

|  | Genotype | Bilirubin (mg/dl) | ALP (U/L) | γ-GT (U/L) | ALT (U/L) | AST (U/L) |
|---|---|---|---|---|---|---|
| CsA | Bsep$^{-/-}$ | 36.4 ± 0.783 (0.193E−10) | 142 ± 1.14 (0.0128) | 1.90 ± 1.96 (0.690) | 59.9 ± 57.5 (0.0783) | 106 ± 54.0 (0.663) |
|  | WT | 1.28 ± 0.262 | 93.2 ± 17.3 | 2.30 ± 0.984 | 11.4 ± 6.16 | 143 ± 102 |
| Normal diet | TKO | 18.2 ± 5.45 (0.193E−03) | 409 ± 131 (0.871E−02) | 1.52 ± 1.47 (0.120) | 56.9 ± 35.9 (0.113) | 150 ± 59.7 (0.584) |
|  | Mdr1a/b$^{-/-}$ | 1.25 ± 0.397 (0.669) | 64.8 ± 9.46 (0.202E−07) | 4.15 ± 2.71 (0.667) | 63.1 ± 64.6 (0.274) | 168 ± 102 (0.509) |
|  | bsep$^{-/-}$ | 0.935 ± 0.197 (0.0392) | 277 ± 117 (0.174) | 2.03 ± 1.01 (0.298) | 58.7 ± 50.1 (0.223) | 71.5 ± 29.5 (0.265) |
|  | WT | 1.35 ± 0.245 | 185 ± 22.0 | 3.42 ± 2.22 | 24.2 ± 8.40 | 126 ± 82.9 |
| CA diet | TKO | 19.4 ± 3.34 (0.890E−08) | 630 ± 121 (0.239E−06) | 1.11 ± 0.521 (0.452) | 300 ± 127 (0.121) | 850 ± 296 (0.0427) |
|  | Mdr1a/b$^{-/-}$ | 0.505 ± 0.125 (0.0848) | 180 ± 31.3 (0.143) | 0.467 ± 0.308 (0.116) | 105 ± 21.0 (0.391) | 179 ± 66.1 (0.322) |

TABLE 1-continued

Liver biochemical indicators in bsep$^{-/-}$, and wildtype female mice treated with Cyclosporine A for two weeks, bsep$^{-/-}$ mdr1a/b$^{-/-}$ Triple Knockout mice, bsep$^{-/-}$, mdr1a/b$^{-/-}$, and wildtype female mice fed a normal diet or fed a 0.5% CA-supplemented diet (n = 4)

| Genotype | Bilirubin (mg/dl) | ALP (U/L) | γ-GT (U/L) | ALT (U/L) | AST (U/L) |
|---|---|---|---|---|---|
| Bsep$^{-/-}$ | 1.47 ± 0.384 (0.250) | 697 ± 216 (0.330E−03) | 0.822 ± 0.749 (0.310) | 405 ± 86.5 (0.505E−02) | 525 ± 139 (0.301) |
| WT | 1.07 ± 0.639 | 205 ± 19.7 | 1.81 ± 1.70 | 157 ± 128 | 344 ± 343 |

ALP—alkaline phosphatase
γGT—γ-Glutamyl Transpeptidase
ALT—Alanine aminotransferase
AST—Aspartate aminotransferase
CA—cholic acid
CsA—cyclosporine A
All numbers are expressed as a mean ± standard deviation (P value) (n = 3-6). Asterisks indicate statistical significance determined by two-tailed Student's t test between the knockout and the wild-type mice in the same group.

Figure 5:
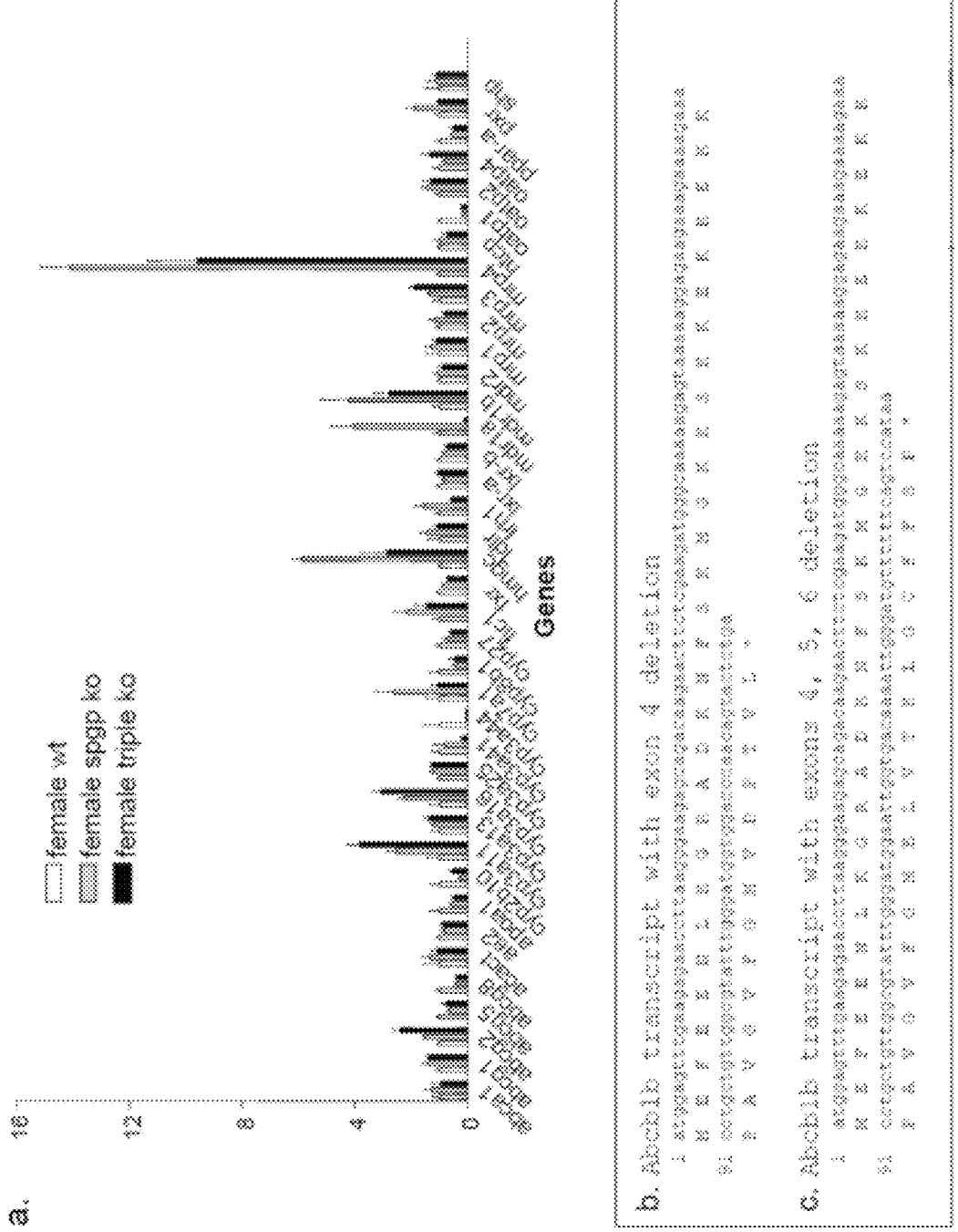
FIG. 5 shows the a) relative mRNA expression of some major liver-expressed genes in wild-type, bsep$^{-/-}$ and TKO mice as determined by semi-quantitative real-time PCR. The mRNA levels were normalized against those of ribosomal protein S15. The level of female wild-type mRNA was set at 1. All numbers are expressed as a ratio of female wild-type mRNA, mean±standard deviation (n=4) (16). b) The major alternatively spliced Mdr1 (Abcb1b) transcript in the TKO mice. This transcript has an exon 4 deletion and results in translation of 38 original amino acids followed by a frame shift, 6 novel amino acids and a premature stop codon. c) The minor Mdr1 (Abcb1b) transcript in TKO mice. This transcript has a deletion of exons 4, 5, and 6 that results in translation of 38 original amino acids followed by a frame shift, 12 novel amino acids and a premature stop codon.

To evaluate the extent of molecular changes in the hepatocytes of the TKO mice, we measured their gene expression profiles using semi-quantitative real-time PCR. TKO mice displayed a typical cholestatic response, similar to what was found in the bsep KO mice (FIG. 5). We found that Mrp3 and Mrp4, the major basolateral bile salt transporters for clearance of bile salt from hepatocytes into the sinusoidal blood circulation, are greatly upregulated, as is the gene most likely to function as the major bile salt hydroxylase, Cyp3a11. Down regulation of Cyp3a41 and Cyp3a44 were also noted. Surprisingly, real-time PCR also detected elevated mdr1 transcription. We sequenced the residual mdr1 transcripts and they consist of two alternatively spliced isoforms, the major one with an exon 4 deletion (SEQ ID NO: 4), directing translation of an N-terminal fragment of 38 amino acids, followed by a frame shift, coding sequence for 7 novel amino acids and a premature stop codon (SEQ ID NO: 5); the less abundant transcript has a deletion of exons 4, 5, and 6 (SEQ ID NO: 6), resulting in translation of 38 original amino acids followed by a frame shift, 12 novel amino acids and a premature stop codon (SEQ ID NO: 7).

Figure 6:
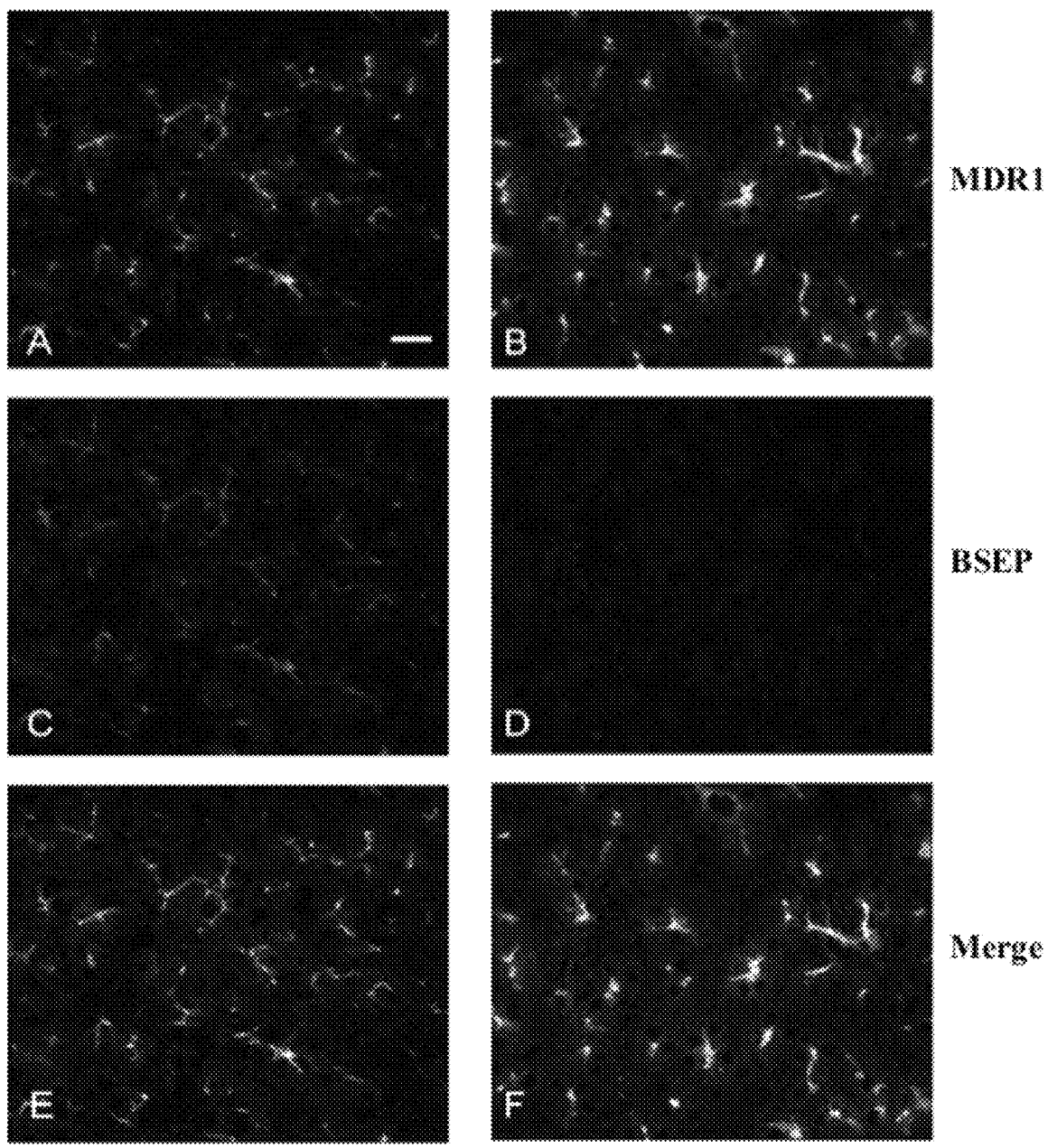
FIG. 6 shows confocal microsopic pictures immunostained for MDR1 or BSEP. MDR1 expression exhibits a strongly canalicular distribution. The lefthand panels are the controls, a liver biopsy from an infant with organic acidemia who did not have jaundice or cholestasis. The right panels are from a liver biopsy sample from a PFIC2 patient.

We also examined the expression of MDR1, along with some other ABC transporters, in PFIC patients of all subtypes. We reasoned that if MDR1 were indeed a physiologically relevant bile salt transporter in humans, intrahepatic bile salt accumulation in PFIC patients should result in MDR1 upregulation. If that were the case, one could stimulate the bile salt transport activity mediated by MDR1 clinically, to alleviate cholestasis. We compared liver biopsies from pediatric PFIC patients from six age-matched controls with non-cholestatic liver diseases, including glycogen storage disease, urea cycle disorders, hepatitis, and a non-tumor liver sample from a hepatoblastoma patient. The controls were not expected to have biliary secretion abnormalities. Assay by quantitative real-time PCR of the biopsy samples revealed a significant increase of MDR1 expression in PFIC patients to approximately four times greater than the average control (Table 2). This increased expression of MDR1 was further confirmed by immunofluorescent staining where a significant increase of human MDR1 protein was detected in the canalicular membrane of the PFIC patients (FIG. 6). The results indicate the presence of a physiologically redundant system for biliary bile salt secretion in both mouse and man.

TABLE 2

Relative expression levels of canalicular transporters in PFIC patients in comparison to age-matched controls

| | age | ABCB1 (MDR1) | BSEP (BSEP) | ABCB4 (MDR3) | ABCC2 (MRP2) | ABCC3 (MRP3) | ABCC4 (MRP4) |
|---|---|---|---|---|---|---|---|
| PFIC-1 | | | | | | | |
| I694N | 10 m | 2.426 | 8.826 | 12.303 | 1.318 | 0.947 | 3.350 |
| 185-282del | 5 m | 3.129 | 9.272 | 11.322 | 1.871 | 0.517 | 4.380 |
| Q1131X/556-628del | 7 m | 1.221 | 12.149 | 12.479 | 0.838 | 0.360 | 16.618 |
| PFIC-2 | | | | | | | |
| V284L/I145T del | 8 m | 1.053 | 2.780 | 5.397 | 1.009 | 1.320 | 2.854 |
| V284L/I145T del | 14 m | 1.327 | 2.638 | 12.887 | 0.843 | 1.511 | 2.198 |
| G1004D/R487H | 8 m | 1.879 | 5.189 | 5.661 | 1.377 | 1.523 | 3.147 |
| PFIC-3 | | | | | | | |
| A* | 5 m | 2.105 | 4.597 | 2.323 | 0.527 | 0.937 | 0.879 |
| B* | 2 m | 2.532 | 2.119 | 1.636 | 0.666 | 0.958 | 4.537 |
| 287-1005del | 6.5 y | 3.300 | 2.979 | 1.346 | 0.960 | 1.540 | 1.899 |
| Paediatric control (n = 6) | | 0.365 ± 0.074 | 3.019 ± 0.466 | 2.071 ± 0.484 | 1.818 ± 0.589 | 0.963 ± 0.279 | 0.729 ± 0.244 |

*PFIC-3 patients diagnosed by their pathological and biochemical presentation.
Relative mRNA levels of transporters are expressed as fold change relative to TBP mRNA levels in each sample (Mean ± SD for controls).

The properties of mutant mice were compared to PFIC2 patients (Table 3).

TABLE 3

| Phenotypes | Bsep KO | Triple KO | PFIC2 |
| --- | --- | --- | --- |
| PGP(MDR1) expression | Very high | no | Very high |
| Liver Size | enlarged | enlarged | Enlarged |
| Bile acids in bile | ¼ of normal | — | <1% of normal |
| Bile flow | Near normal | blocked | — |
| Jaundice | no | severe | severe |
| GGT | normal | low or normal | low or normal |
| ALP/ALT/AST | normal | high | high |

A significant upregulation of MDR1 expression was found in livers of PFIC patients.

EXAMPLE 2

Synthesis of taurine-conjugated 3α,6β,7β,12α-hydroxy bile acid

A taurine-conjugated 3α, 6β, 7β, 12α-hydroxy bile acid, essentially a 12α-hydroxylated version of β-muricholate, is synthesised as set out in (29-31). Isomers are produced simultaneously in the synthesis, and are likely to have similar activities. Therefore, at least five additional derivatives, specifically 3α, 6α, 7α, 12α-; 3α, 6β, 7α, 12α-; 3α, 6α, 7β, 12α-; 3α, 6β, 7β, 12α-; 3α, 6α, 7α, 12β-hydroxy derivatives of the above compound are also isolated. The isolated compounds are labeled using is $^3$H-labelling bile salts by hydrogen exchange in a solution of tritium-enriched water, followed by re-isolation of the labeled bile salt (a service available from Perkin-Elmer, for example) (32). The isolated compounds are tested for their relative affinities for transport via MDR1 in vitro, as described herein. The most efficacious compound in vitro is isolated in larger quantities and used as the lead compound for the in vivo tests of toxicity and efficacy described herein or known in the art.

1. Synthesis of taurine-conjugated 3α,6α,7α,12α-tetrahydroxy-5β cholanoic acid

Figure 10:
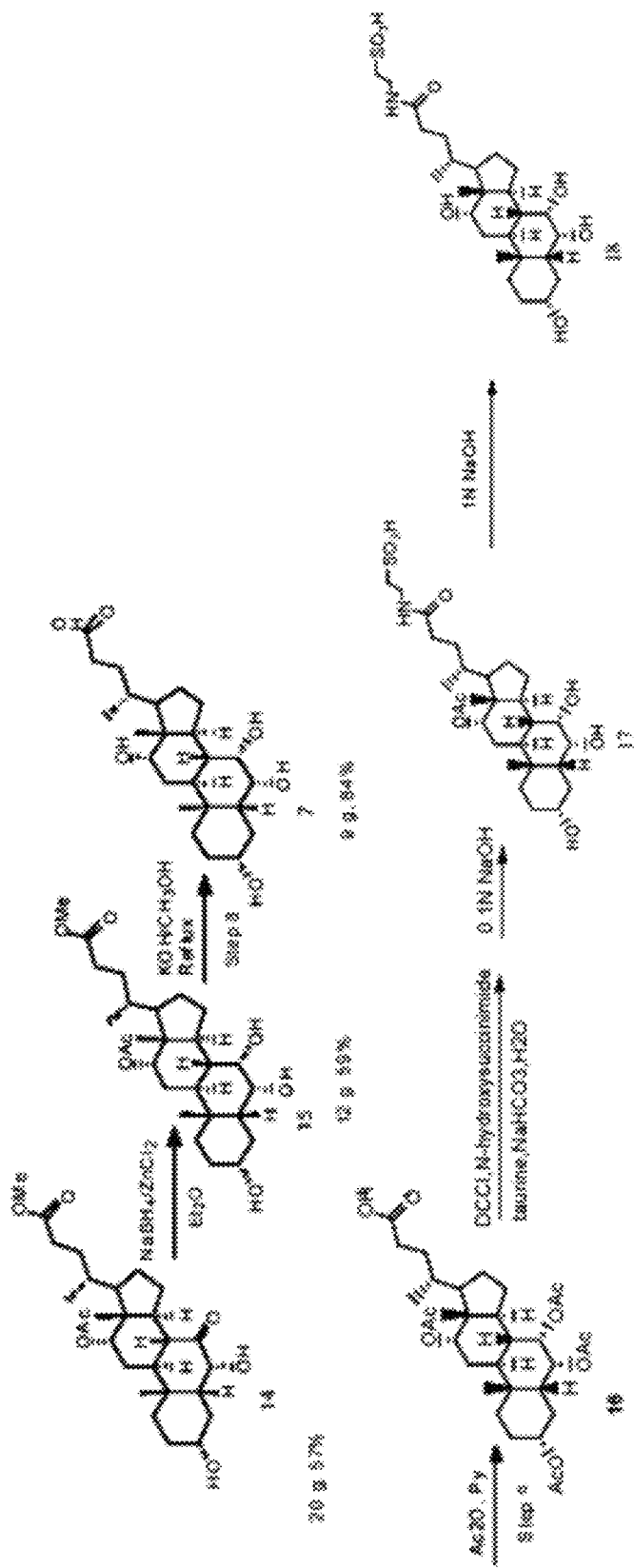
FIG. 10 shows synthetic steps for production of taurine-conjugated 3α,6α7α12α-tetrahydroxy-5β-cholanoic acid.
Figure 11:
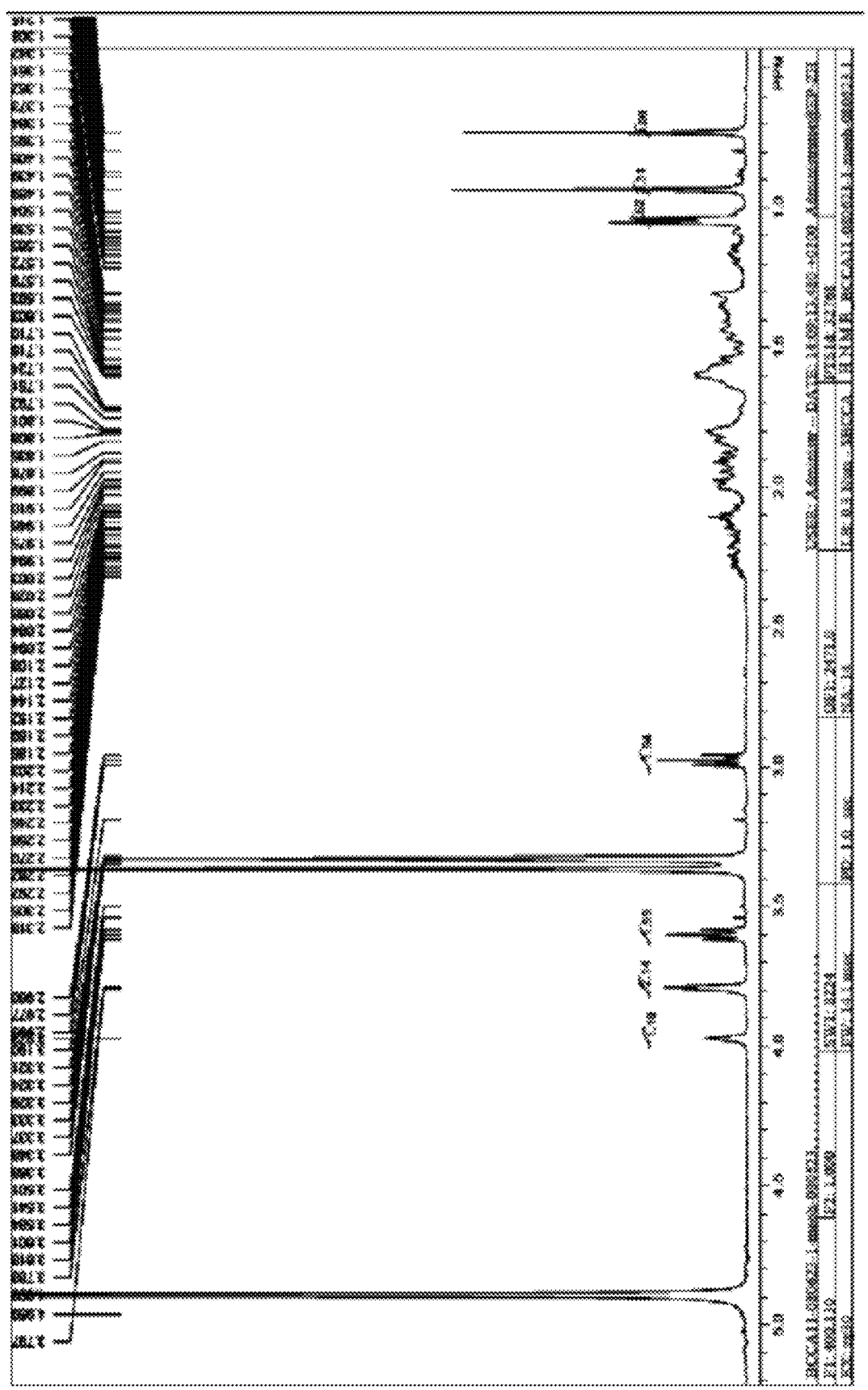
FIG. 11 shows 1H-NMR spectrum of taurine-conjugated 3α,6α7α12α-tetrahydroxy-5β-cholanoic acid (18), produced by the method shown in FIG. 10.

Referring to FIG. 10, 3α,6α,7α,12α-tetrahydroxy-5β-cholanoic acid (7) was protected as an acetate (16). Under an N$_2$ atmosphere, taurine was activated with N-hydroxysuccinimide in the presence of organic base and acetate (16), worked up with 0.1 N NaOH and washed through Serdolit™-1, to provide amide (17). Amide (17) was treated with 1 N NaOH, for 40 minutes at 80° C., followed by 20 minute at 50° C., and 1.5 hr at 25° C.; yielding taurine conjugate (18) after washing through Serdolit™-1. $^1$H-NMR spectrum of taurine conjugated 3α,6α,7α,12α-tetrahydroxy-5β cholanoic acid (18) is shown in FIG. 11.

EXAMPLE 3

Evaluation of Transport Kinetics and Interactions

The transport kinetics and interactions of compounds, produced as described herein, with their transporter MDR1, are evaluated in comparison to the widely used therapeutic bile acid ursodeoxycholate as well as taurocholate, the primary bile acid in humans and mice and β-muricholate, a tri-hydroxy bile acid not normally found in humans. Membrane vesicle systems derived from CHO B30 cell membranes, a line of Chinese Hamster Ovary cells selected for its considerable amplification of the Mdr1 locus and corresponding drug resistance are used, as well as vesicles from the human SKOV series of cell lines, also selected for MDR1 overexpression. This experimental system is well established. Using this system ATP-dependent uptake of $^3$H-labeled bile acids into vesicles, either alone or in combination with interacting compounds such as taurocholate or ursodeoxycholate, is measured. Humans and rodents do not differ significantly in the drug-resistance profiles mediated by their respective MDR1 P-glycoproteins, therefore using both human and rodent-cell derived vesicles confirms that any differences in novel bile acid transport kinetics between the species does not significantly alter their expected utility. Any bile acid less hydrophobic (and therefore less toxic) than taurocholate, but with a higher affinity than taurocholate (lower $K_m$) for transport by MDR1 is of potential therapeutic benefit e.g., tetrahydroxylated bile acids show a suitable mix of low-toxicity and high capacity for transport by MDR1.

Modulation of transporter affinity for bile salts is also a mechanism by which muricholates and tetra-hydroxylated bile acids overcome cholestasis. A bile acid according to the invention may allosterically reduce the $K_m$ of MDR1 for cholate, and so further increase its value as a choleretic agent. Such effects on MDR1 are examined using isolated membrane vesicles in the presence of the various bile acids and also potential stimulators such as rhodamine 123, Hoechst 33342 or prazosin, known to interact with Mdr1 at separate sites (33-35). Uptake kinetics of commercially available $^{14}$C-taurocholate into B30 membrane vesicles in the presence of various concentrations of potential modulators are compared. Positive modulation increases the uptake rate. Drugs known to be Mdr1 substrates are screened. Drug-bile acid and bile acid-bile acid interactions are characterized to determine if the $K_m$ for taurocholate transport has decreased.

EXAMPLE 4

Determination of Maximum Tolerated Dose In Vivo

The maximum tolerated dose of bile acid according to the invention is determined. This test is carried out in two ways. First, as a pilot experiment of bile duct cannulation, a bolus of bile acid was infused into mice under anesthesia to measure its acute toxicity to animals. The responses of mice such as breath rate, bile flow rate, histological changes by H&E staining and the like were recorded. For taurocholate our tests indicated that 167 μmol/kg of body weight delivered intravenously, was the maximum tolerated dosage. Using this tolerance level as a reference point, the acute toxicity of the bile acid is determined. The maximum tolerated dosage (MTD) for intravenously administered ursodeoxycholate was found to be 65 μmol/kg of body weight.

Therapeutic doses of ursodeoxycholate in humans are usually given orally and typically do not exceed 40 μmol/kg/of body weight per day. Further, orally administered bile acid may be less toxic as it enters the bloodstream and thus the liver at a slower rate than would occur with intravenous administration. The oral LD50 for ursodeoxycholate in rodents is at least 15 times greater than when given intravenously, giving considerable safety margin against overdose. Bile acids showing even greater affinity for Mdr1 than muricholates or cholates have a greater dose-specific effect on enhancing bile flow under conditions of Bsep dysfunction, while demonstrating lower toxicity at any given dose.

Chronic toxicity is tested by supplementing the diets of mice (wild-type as well as the hypersensitive bsep KO mice) with 0.1%-0.5% β-muricholate or bile acid according to the invention. Control feeding experiments use cholate as well as ursodeoxycholate. Wild-type mice can endure the extra bile salt loading of a 0.5% cholate indefinitely, while the same diet will cause female bsep KO mice to lose weight, and kills male bsep KO mice within 10 days (16, 18). A 0.5% cholate diet will kill even female TKO mice within a week (36). Animals are fed control and bile acid-supplemented diets and monitored daily for weight loss and weekly for serum indicators of liver function to detect symptoms of cholestasis such as elevated liver enzymes in blood, as well as elevated bile salts and/or bilirubin (Table 1). Bile duct cannulations are also conducted in which a bolus of $^{14}C$-taurocholate is injected into the tail veins of mice, either alone or together with a novel bile acid, and the kinetics of $^{14}C$-taurocholate appearance in the bile measured and the in vivo effect of each novel bile acid upon taurocholate transport by Mdr1 and/or Bsep is evaluated.

EXAMPLE 5

Amelioration of Cholestasis In Vivo

The effectiveness of bile acids according to the invention is assessed in a whole animal system that allows the influence of molecular and physiological events affecting bile salt transport and bile flow. A combination of unique knockout mouse lines is used to test whether the novel bile salts can alleviate the cholestatic stress by promoting Mdr1-mediated bile flow. Three lines of KO mice are used. As described herein, the bsep KO mouse carries an inactivated bsep gene but has elevated mdr1a/1b expression; the mdr1a/mdr1b double KO mouse have normal bsep expression but inactivated mdr1a/1b genes; and the bsep/mdr1a/mdr1b triple KO mouse (TKO) has all three genes inactivated. These three lines of animals are used to verify the in vivo choleretic function of the novel bile acid in alleviating cholestatic pressure.

Small amounts of $^{3}H$-labelled THBAs, of various isomers, prepared as described herein, are injected into the mutant mouse strains (plus wild-type controls), and radioactivity recovered in blood, urine, bile and hepatocytes are measured in order to compare the in vivo kinetics of the novel THBAs to those obtained for the same compounds in vitro, as described herein. The mice are challenged with a high dose of a bile acid according to the invention, selected on the basis of the kinetic experiments described above. Concentrations of 0.5%-1.5% are used in the diet, given that the same amount of taurocholate (a substrate preferred by Bsep) can be tolerated indefinitely by wild-type mice. The mice are monitored according to their body weight, morbidity, mortality, liver indicator profile, and liver histology as reported previously (16, 18, 37) (Table 1). In addition, the bile of animals being fed the bile acid according to the invention is collected, and analyzed by HALC. Increase in the amount of bile flow is a direct measure of the choleretic potential of the bile acid according to the invention, and changes in the bile acid composition of bile in the three KO mouse strains indicate the extent to which bile acid according to the invention is transported by Mdr1 versus Bsep in vivo. Changes in the proportions of biliary bile acids other than the bile acid according to the invention itself, if observed, indicate modulatory effects of the bile acid according to the invention on the transport or synthesis of the conventional bile acid pool.

High dose feeding has fewer negative effects than taurocholate on bsep KO mice, moderate toxicity towards mdr1a/1b mice and high toxicity for TKO mice. Previously, we have found that bsep KO and TKO mice are hypersensitive to taurocholate feeding. If feeding with the novel bile acid according to the invention is less toxic to bsep KO mice than taurocholate feeding, we will then challenge our mutant mice with mixtures of the bile acid according to the invention and cholate or ursodeoxycholate in order to provide direct in vivo evidence for the therapeutic value of the bile acid according to the invention.

EXAMPLE 6

Synthesis of 3α,6α,7α,12α-tetrahydroxy-5β-cholanoic acid and 3α,6β,7α,12α-tetrahydroxy-5β-cholanoic acid Three forms of bile acid were synthesized: 3α,6α,7α,12α-tetrahydroxy-5β-cholan-24-oic acid, 3α,6β,7α,12α-tetrahydroxy-5β-cholan-24-oic acid and 3α,6β,7α,12α-tetrahydroxy-5β-cholan-24-oic acid. The following syntheses are based on those reported by Iida et al. and Aggarwal et al. (61, 62, and references cited therein), and Gouin et al., Fieser et al., Putz et al., Narasimhan et al. and Ornatein et al. (66-70 and references cited therein). This chemistry has been performed on a multi-gram scale and minor modifications have been made to the experimental and purification procedures in order to optimize yields. The final compounds were purified by flash chromatography and were greater than 95% pure (as indicated by NMR analysis). They have also been shown to be homogeneous by HPLC methods.

Synthesis of 3α,6α,7α,12α-tetrahydroxy-5β-cholanoic acid

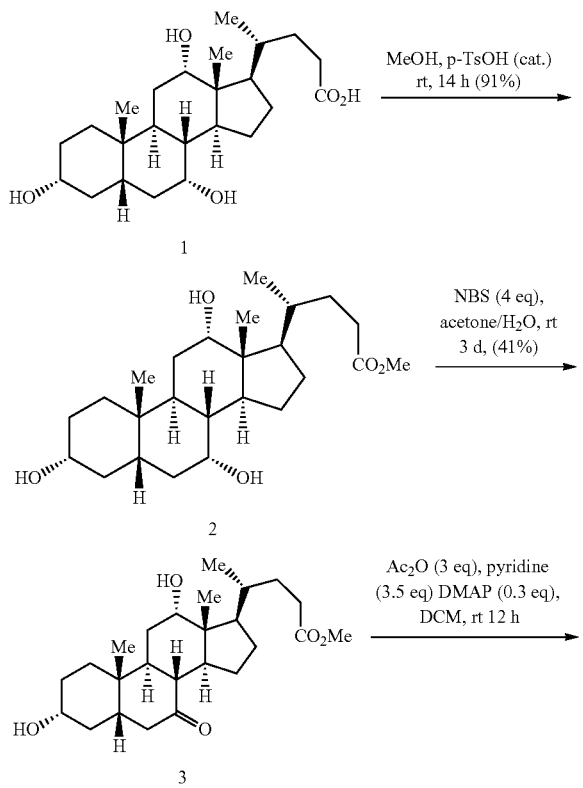

and global deprotection of the acetate and methyl ester moieties afforded the target compound (7).

Synthesis of 3α,6β,7α,12α-tetrahydroxy-5β-cholanoic acid

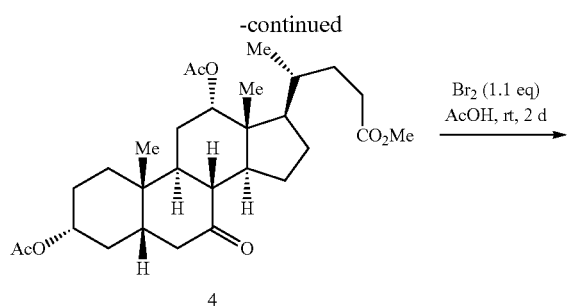

4

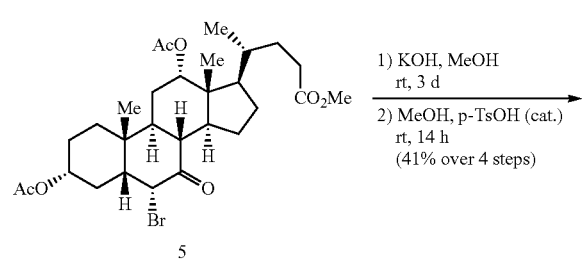

5

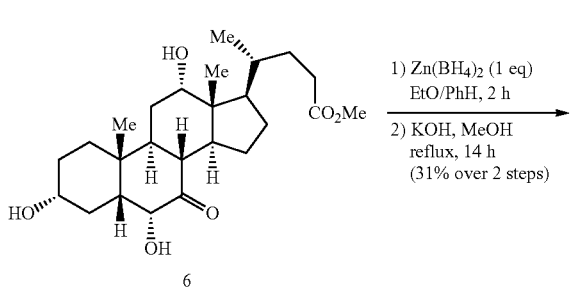

6

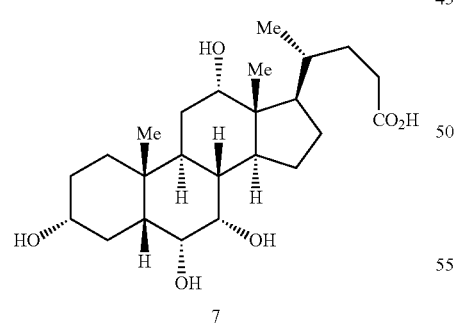

7

3α,6α,7α,12α-tetrahydroxy-5β-cholanoic acid

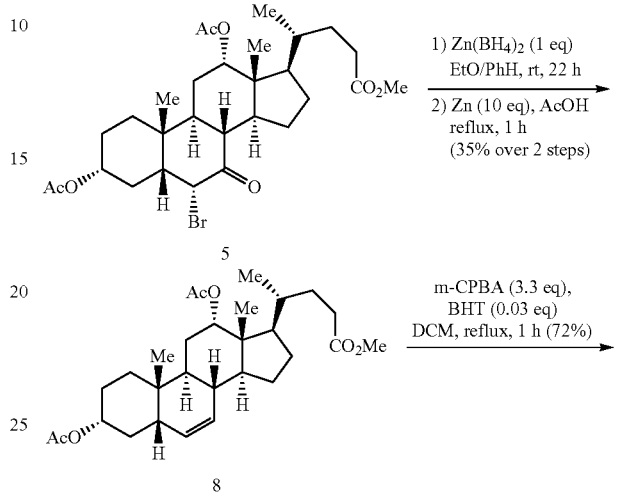

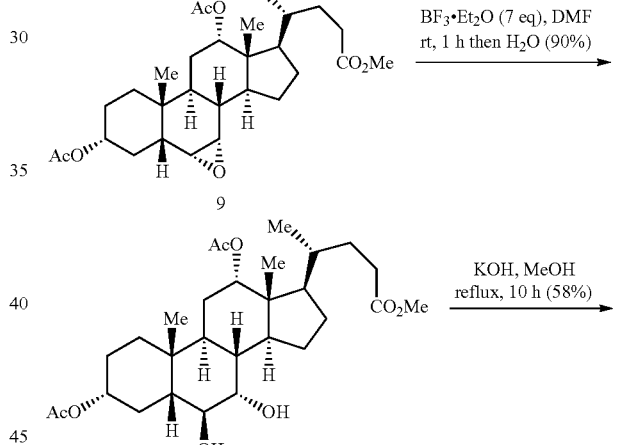

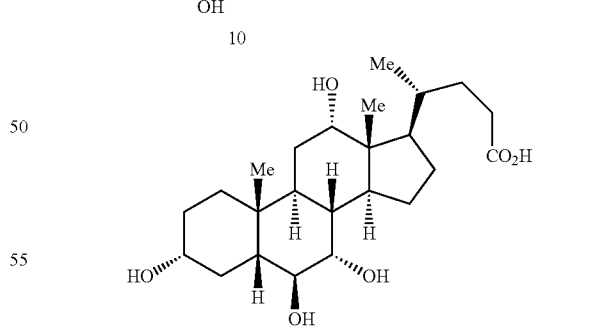

11

3α,6β,7α,12α-tetrahydroxy-5β-cholanoic acid

Protection of cholic acid (1) afforded the methyl ester (2) that was oxidized with N-bromosuccinimide (NBS) to the corresponding ketone (3). This compound was then protected as the diacetate (4) and converted to the key intermediate (5) on reaction with molecular bromine. This bromide was then hydrolyzed to the hydroxyl-ketone (6). Subsequent reduction The intermediate (5), see above, was reduced with zinc borohydride and the resultant bromohydrin was reduced further with metallic zinc to afford the corresponding alkene (8). Treatment of the latter compound with meta-chloroperoxybenzoic acid (m-CPBA) afforded the epoxide (9). Lewis acid-mediated ring opening of this compound afforded the diol (10). Subsequent global deprotection afforded the target compound (11).

Alternate method of synthesis of 3α,6α,7α,12α-tetrahydroxy-5β-cholanoic acid

Figure 9:
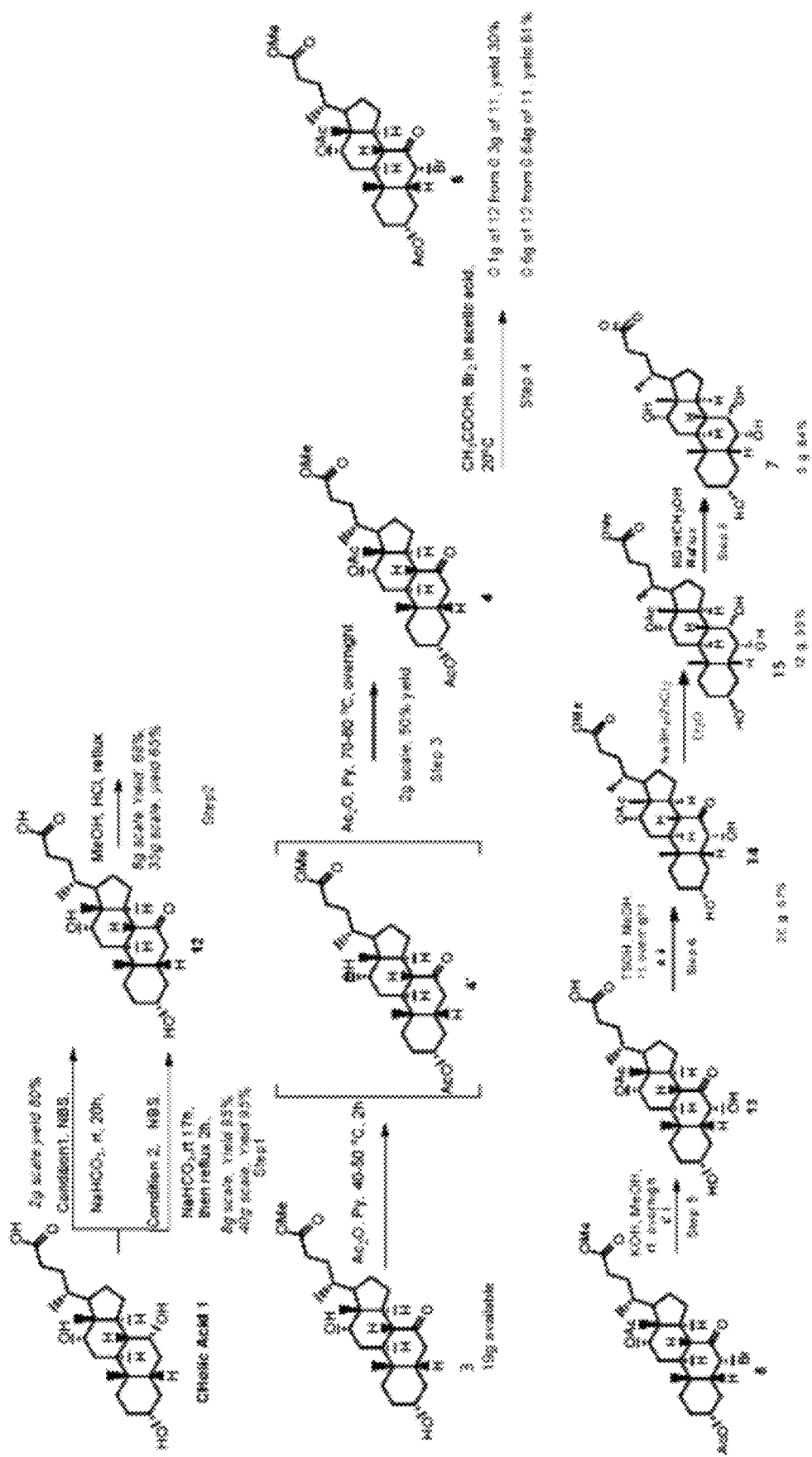
FIG. 9 shows synthetic steps for production of 3α,6α,7α,12α-tetrahydroxy-5β-cholanoic acid (6α, 7α THBA) from cholic acid.

Referring to FIG. 9, oxidation of cholic acid (1) with NBS provided corresponding ketone (12) followed by protection to afford the corresponding methyl ester (3). This compound was then protected as an acetate (4'), and subsequently, acetate (4) and converted to intermediate (5) by reaction with molecular bromine. The bromide was hydrolyzed to the hydroxyl-ketone (13). Subsequent reduction and deprotection afforded the target compound (7).

EXAMPLE 7

3α,6α,7α,12α-tetrahydroxy-5β-cholan-24-oic acid stimulates bile flow rate (BFR) in wild-type mice For bile duct cannulation, wild type mice on the genetic background of FVB/NJ were weighed and anesthetized by intraperitoneal injection of Ketamine (112.5 mg/kg) and Xylazine (11.3 mg/kg) after 2-4 hours of fasting. The abdomen was opened, and the gall bladder was cannulated using a PE-10 catheter after distal common bile duct ligation [63, 64]. After 20 minutes of bile flow equilibration, bile was collected into pre-weighed tubes at 5-minute intervals for 10 minutes. A bolus of 3α,6α,7α,12α-tetrahydroxy-5β-cholan-24-oic acid (6α, 7α THBA, pH. 7.4-7.6), 3α,6β,7α,12α-tetrahydroxy-5β-cholan-24-oic acid (6β, 7α THBA, pH. 7.4-7.6), ursodeoxycholic acid (UDC, pH. 7.4-7.6) or cholic acid (100 μmol/kg body weight) was then infused into the tail vein over a 20-second interval. Bile was then further collected through the cannula at 2-minute intervals for 10 or 20 minutes, followed by 10-minute intervals for 30 minutes. The bile flow rate was calculated by weighing the tubes containing the collected bile. Bile collected was used for HPLC analysis.

UDC solution for the infusion was freshly made within 2 hours prior to the experiments, and was made as follows: for each milliliter of 100 mM UDC solution, 39.62 mg of UDC (Sigma U5127) was vortex-mixed in sequence with 86.6 μl of 100% ethanol, 86.6 μl of 1N NaOH, and 826 μl of 0.9% NaCl solution. Different working solution are diluted from the 100 mM solution. The pH of the solution was 7.4-7.6.

Figure 7:
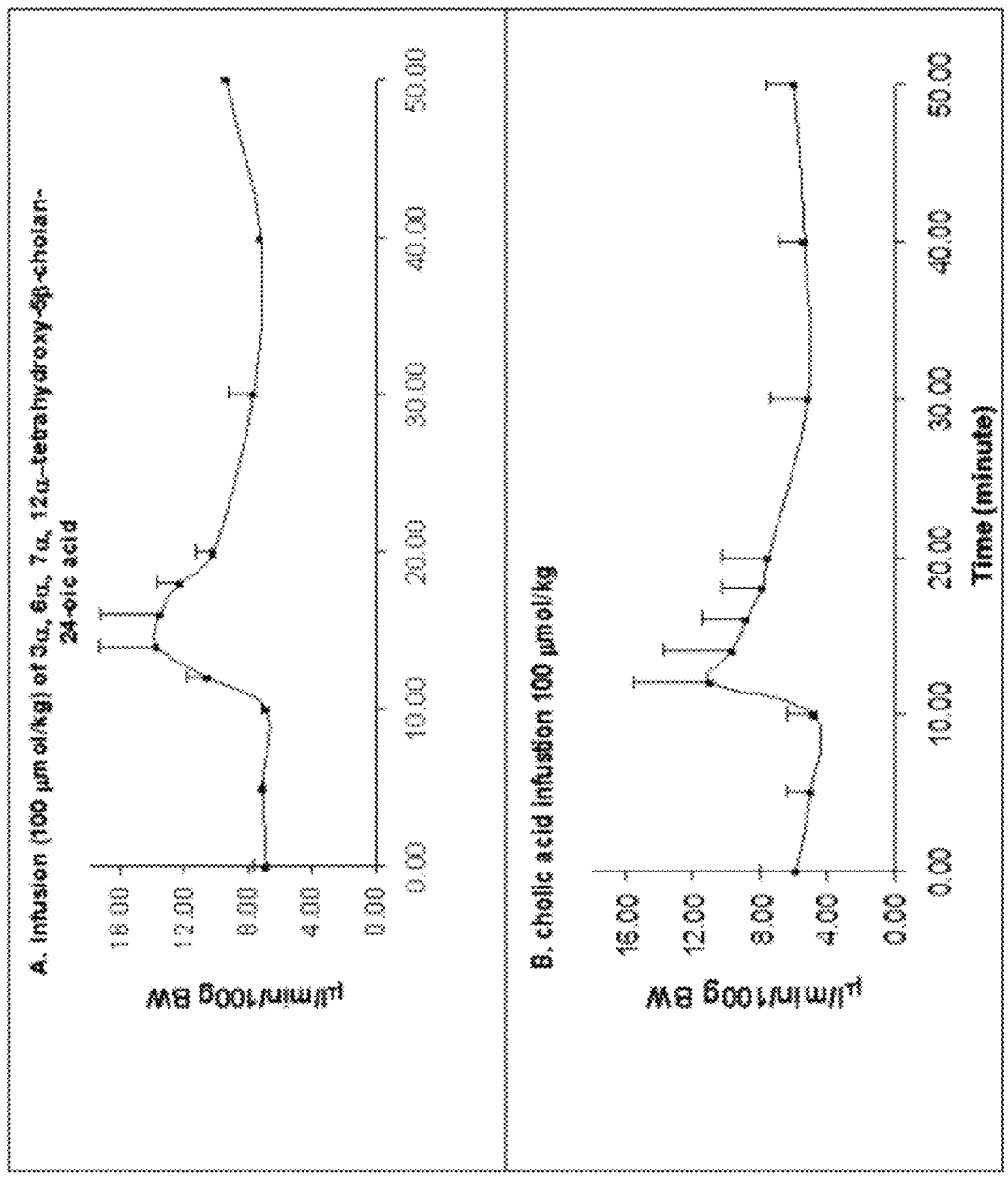
FIGS. 7A-B show that 3α,6α,7α,12α-tetrahydroxy-5β-cholan-24-oic acid stimulates bile flow rate (BFR) in wild-type mice. (A) BFR as a function of body weight in mice after infusion of 3α,6α,7α,12α-tetrahydroxy-5β-cholan-24-oic acid (6α,7α THBA). (B) BFR as a function of body weight in mice after infusion of cholic acid (CA) (3α,6α,7α,12α-trihydroxy-5β-cholan-24-oic acid).

FIG. 7 demonstrates that 3α,6α,7α,12α-tetrahydroxy-5β-cholan-24-oic acid stimulates bile flow rate (BFR) in wild-type mice. (A) BFR as a function of body weight in mice after infusion of 3α,6α,7α,12α-tetrahydroxy-5β-cholan-24-oic acid (THBA). (B) BFR as a function of body weight in mice after infusion of cholic acid (CA) (3α, 7α,12α-trihydroxy-5β-cholan-24-oic acid). A bolus of THBA or CA (100 μmol/kg body weight) was infused into the tail vein over a 20 second interval at 10 minutes. Results are presented as the mean (μl/100 g of body weight)±the standard deviation.

Bile flow rate (BFR) was determined before and after infusion of 3α,6β,7α,12α tetrahydroxy cholanoic acid (6β, 7αTHBA) at a dose of 65, 250, 350 and 400 mmol/kg body weight (BW) (FIG. 12A); or infusion of 3α, 6α 7α 12α THBA (6α, 7α THBA) of 65 and 200 mmol/kg BW (FIG. 12B). FIG. 12C illustrates BFR as a function of body weight before and after the infusion of 65 mmol/kg body weight of 6β, 7αTHBA, 6α, 7α THBA and ursodeoxycholic acid (UDC). Results are represented as the mean±the standard deviation of three mice.

During bile duct cannulation experiments, we have found that UDC infused through the tail vein at a concentration of 70 mmol/kg body weight or higher caused death of wild-type mice under anesthesia (Ketamine, 112.5 mg/kg and Xylazine, 11.3 mg/kg). We thus determined that UDC at 65 mmol/kg of body weight as administrated through a bolus tail vein infusion was the maximum tolerated dose (MTD) in the mice. However, the wild-type mice can tolerate 6β, 7α THBA infusion at 500 μmol/kg of body weight (highest dosage tested) and 6α, 7α THBA infusion at 400 mmol/kg of body weight (highest dosage tested) without death. The maximum tolerated doses of 6β, 7αTHBA (MTD>500 μmol/kg of body weight) and 6α, 7α THBA (MTD>400 μmol/kg of body weight) were several times higher than that of UDC.

UDC at 65 μmol/kg body weight is the maximum tolerated dose (MTD) in the mice, resulting in a bile flow rate similar to that observed by infusion of a similar quantity of 6β, 7αTHBA or 6α, 7α THBA. Infusion of increasing quantities of 6β, 7αTHBA or 6α, 7α THBA, results in a corresponding increase in bile flow rate (FIGS. 12 A, B).

Figure 8:
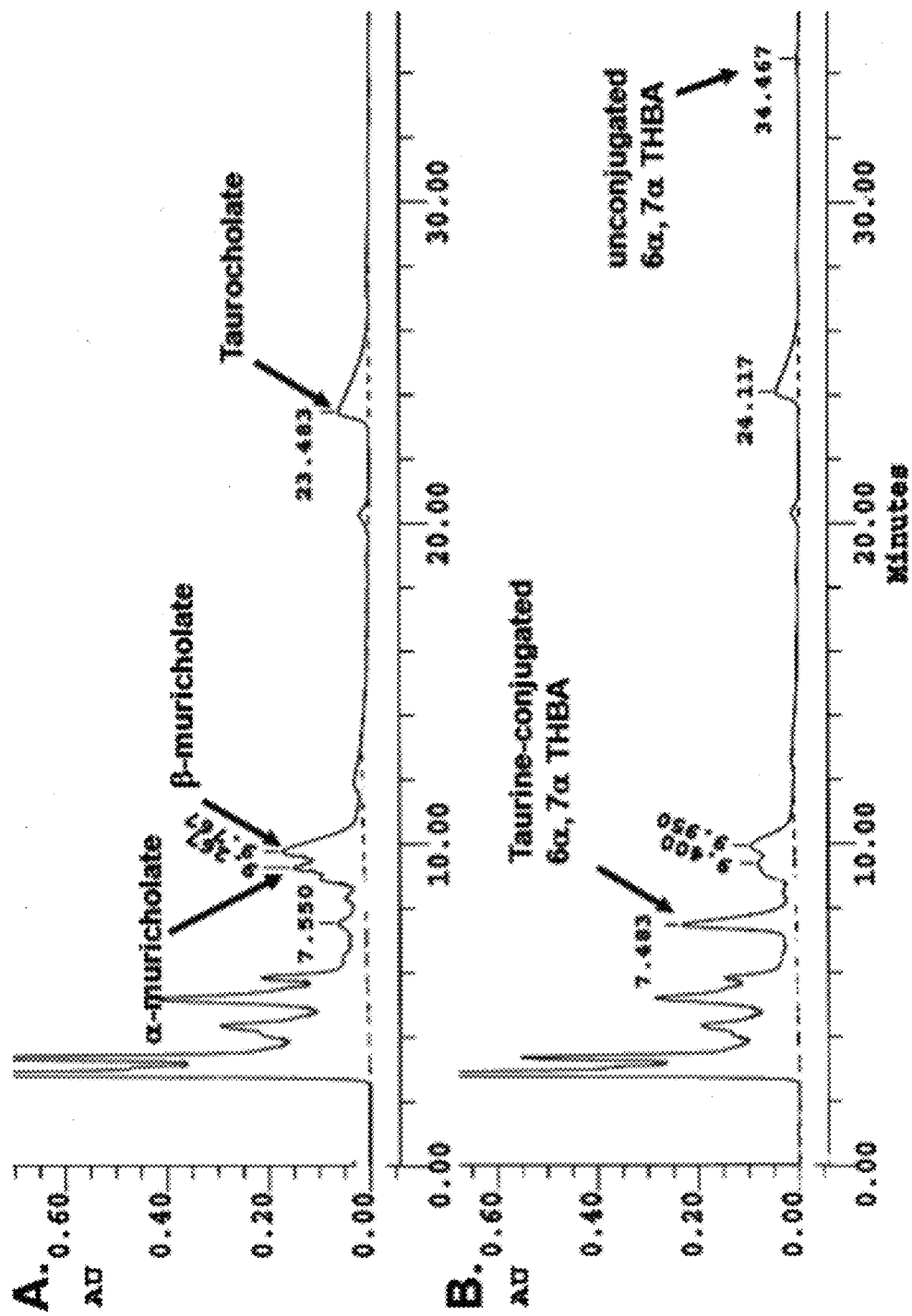
FIG. 8 A-B shows HPLC (High Performance Liquid Chromatography) profiles of bile salt in the bile of a male wild type mouse before (A) and after (B) infusion of unconjugated 3α,6α,7α,12α-tetrahydroxy-5β-cholan-24-oic acid (6α,7α THBA, 100 mol/kg as a function of body weight). (C) shows HPLC profiles of bile fractions collected from a wild-type mouse before (upper trace), and 2-4 minutes after (lower trace), infusion (100 μmol/kg) of cholic acid (3α,7α,12α-trihydroxy-5β-cholan-24-oic acid). The bile samples were collected from a wild type mouse by bile duct cannulation. Equal volumes of bile were loaded.
Figure 8:
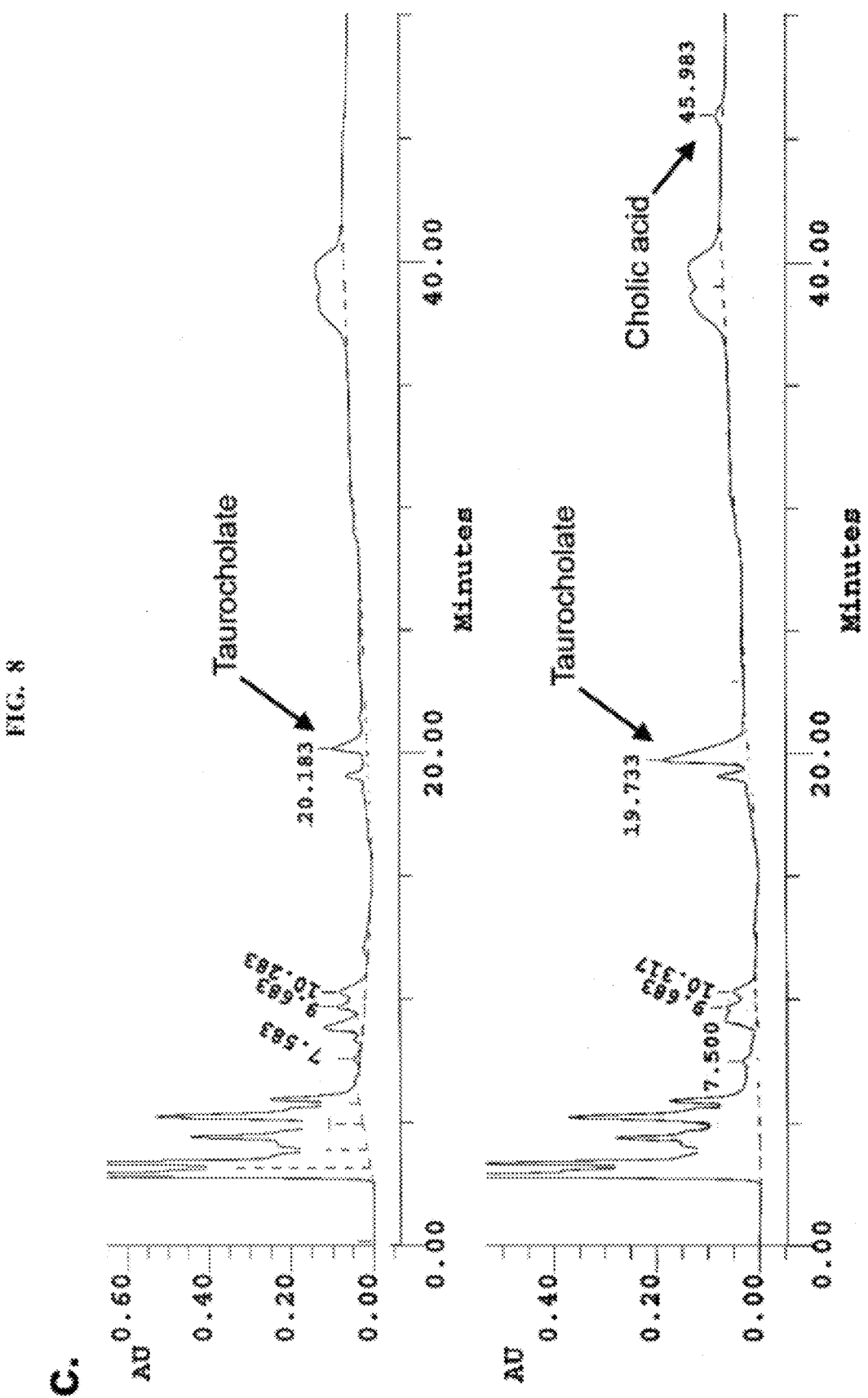

FIG. 8 demonstrates HPLC (High Performance Liquid Chromatography) profiles of bile fractions collected from a wild-type mouse before (A), and 2-4 minutes after (B), infusion (100 μmol/kg) of 3α,6α,7α,12α-tetrahydroxy-5β-cholan-24-oic acid. FIG. 8C shows HPLC profiles of bile fractions collected from a wild-type mouse before (upper trace), and 2-4 minutes after (lower trace), infusion (100 mmol/kg) of cholic acid.

HPLC was carried out with a Waters 600 pump and controller and a 486 UV detector. Separation was performed on a Spherisorb S5 ODS2 C-18 (5 mm particle size, 250 mm×4 mm, Waters) reverse phase analytical column and was preceded by guard column (Nova Pack, Waters). Integration of the peaks was carried out using Millennium 2010 software. The bile salt controls were separated at ambient temperature over 48 minutes at a flow rate of 0.6 mL/min and 3200 psi. The mobile phase consisted of solvent A (MeOH) and solvent B (60:40 MeOH: 0.01 M potassium phosphate, 0.02 M sodium phosphate (pH 5.35 (modified from Rossi et al. 1987 *J Lipid Res* 28(5): 589-95 (71); Hagey et al. 1998. *J Lipid Res* 39(11): 2119-24, (72)). Initial conditions were held at 100% B for the first 25 minutes. Over the next 10 minutes, there was a linear gradient to 30% B and conditions were held for another 5 minutes. The conditions then decreased through a linear gradient to 100% A over 8 minutes. The system was flushed with 100% MeOH followed by equilibration back to the initial conditions. The effluent was monitored at 210 nm.

For visualizing the 3α,6α,7α,12α-THBA, 4 μl bile was dissolved in 20 μl methanol, and injected into a buffer stream at 0.6 mL/minute, and read by absorbance at a wavelength of 210 nm. The buffer was 60% methanol, 40% 0.1M $KH_2PO_4$, 0.02M $NaH_2PO_4$ pH5.35 [65]. For visualizing cholic acid, the procedure was the same as for 3α,6α,7α,12α-THBA initially, but after 5 minutes the buffer was stepped linearly to a mixture of 20% methanol:80% buffer within 4 minutes, held constant for another 10 minutes, then stepped linearly within 2 minutes to 30% methanol:70% buffer for the duration of the run.

Therefore, tetrahydroxy-5β-cholan-24-oic acids (3α,6α, 7α,12α-tetrahydroxy-5β-cholan-24-oic acid) promotes bile flow in wild-type mice. As demonstrated by High Performance Liquid Chromatography (HPLC), 3α,6α,7α,12α-tetrahydroxy-5β-cholan-24-oic acid is metabolized by taurine-conjugation in vivo and secreted into the bile minutes after being infused into the mouse tail vein (FIG. 8A, B). This suggests that this bile acid can be metabolized and detoxified by the same pathways that metabolize native bile acids and mediate their secretion across the canalicular membrane.

EXAMPLE 8

Synthesis of 2α,3α,7α,12α-tetrahydroxy-5β-cholanoic acid and 3α,6α,7α,12α-tetrahydroxy-5β-cholanoic acid 2α,3α,7α,12α-tetrahydroxy-5β-cholanoic acid was synthesized from cholic acid as follows:

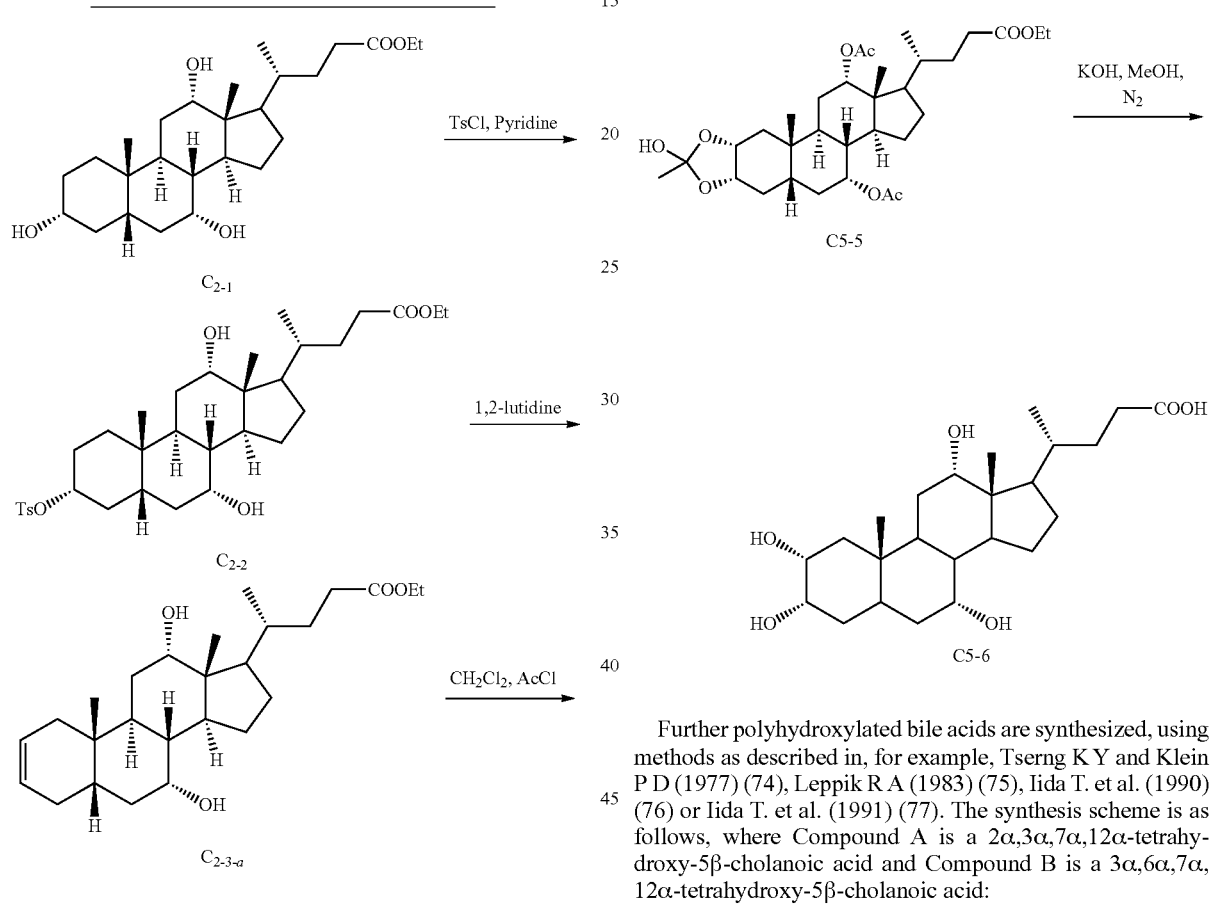

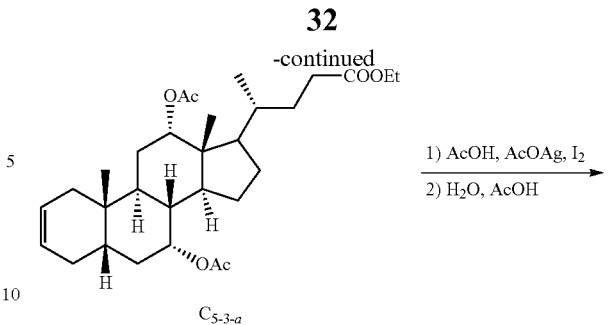

Further polyhydroxylated bile acids are synthesized, using methods as described in, for example, Tserng K Y and Klein P D (1977) (74), Leppik R A (1983) (75), Iida T. et al. (1990) (76) or Iida T. et al. (1991) (77). The synthesis scheme is as follows, where Compound A is a 2α,3α,7α,12α-tetrahydroxy-5β-cholanoic acid and Compound B is a 3α,6α,7α,12α-tetrahydroxy-5β-cholanoic acid:

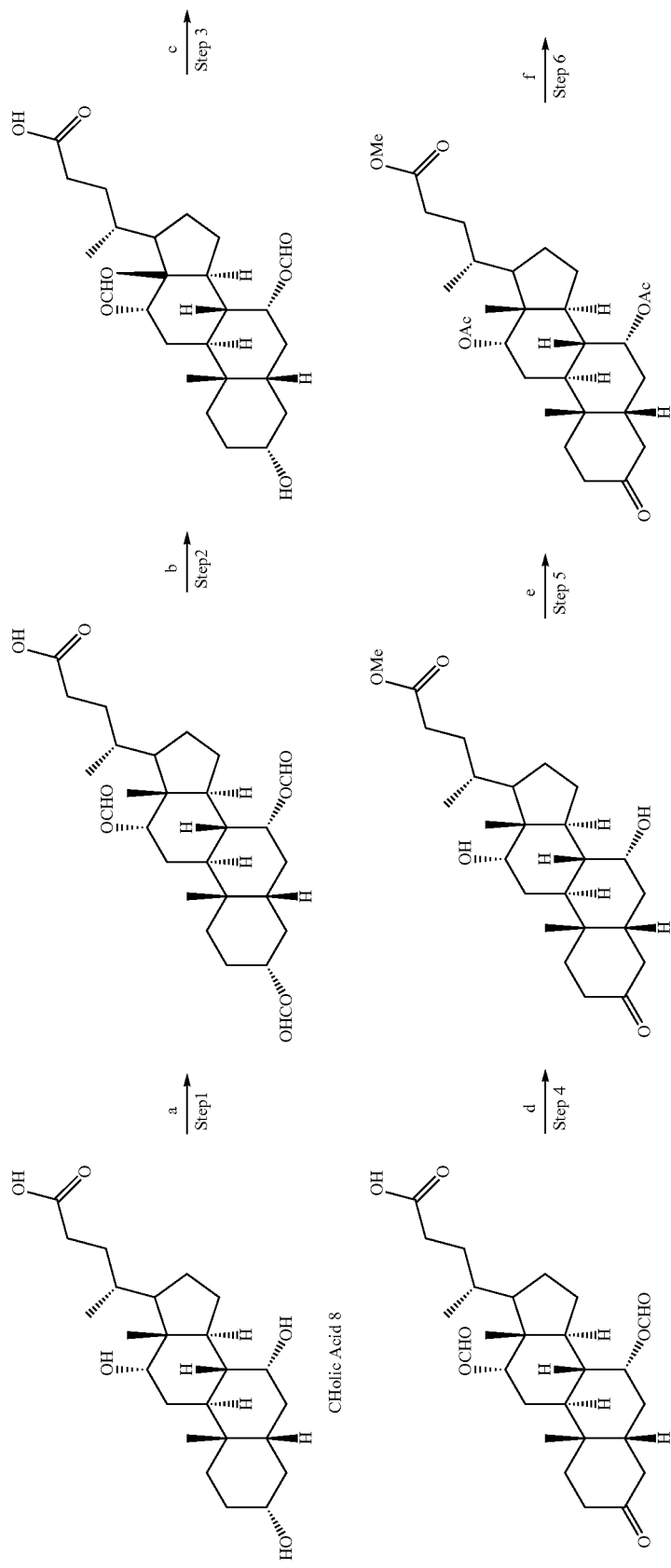

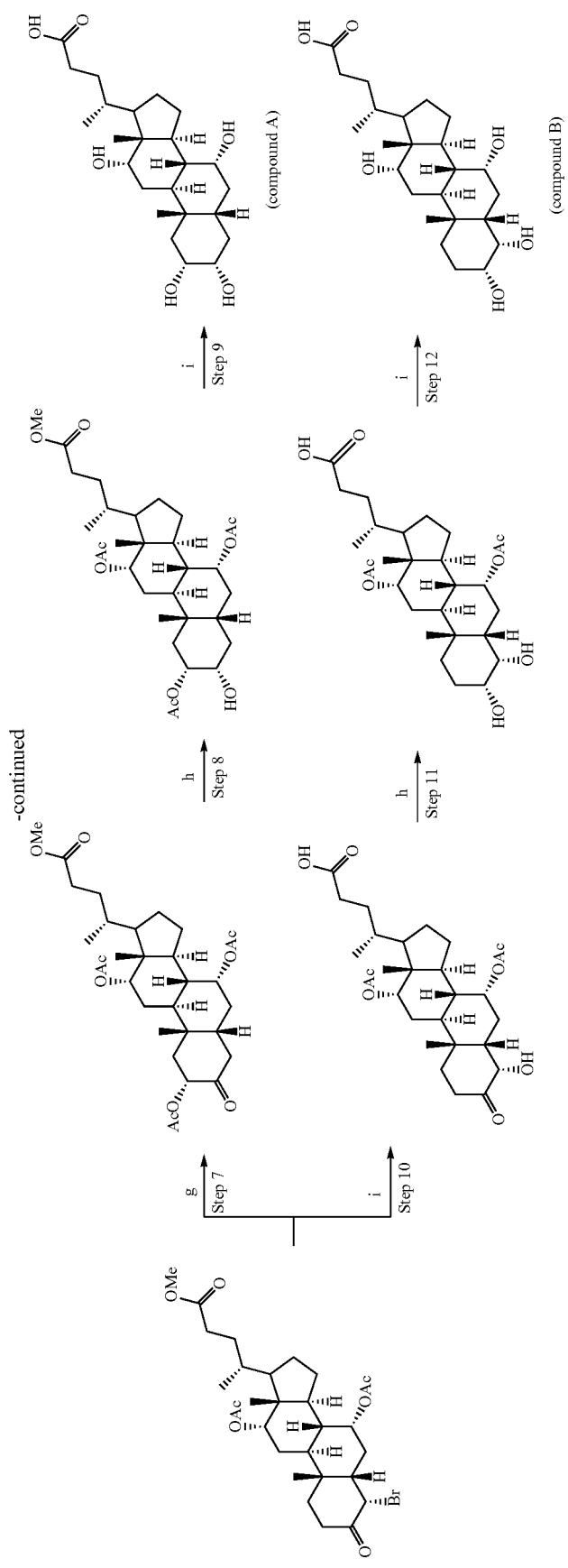

An alternate synthesis scheme for 3α,6α,7α,12α-tetrahydroxy-5β-cholanoic acid is as follows:

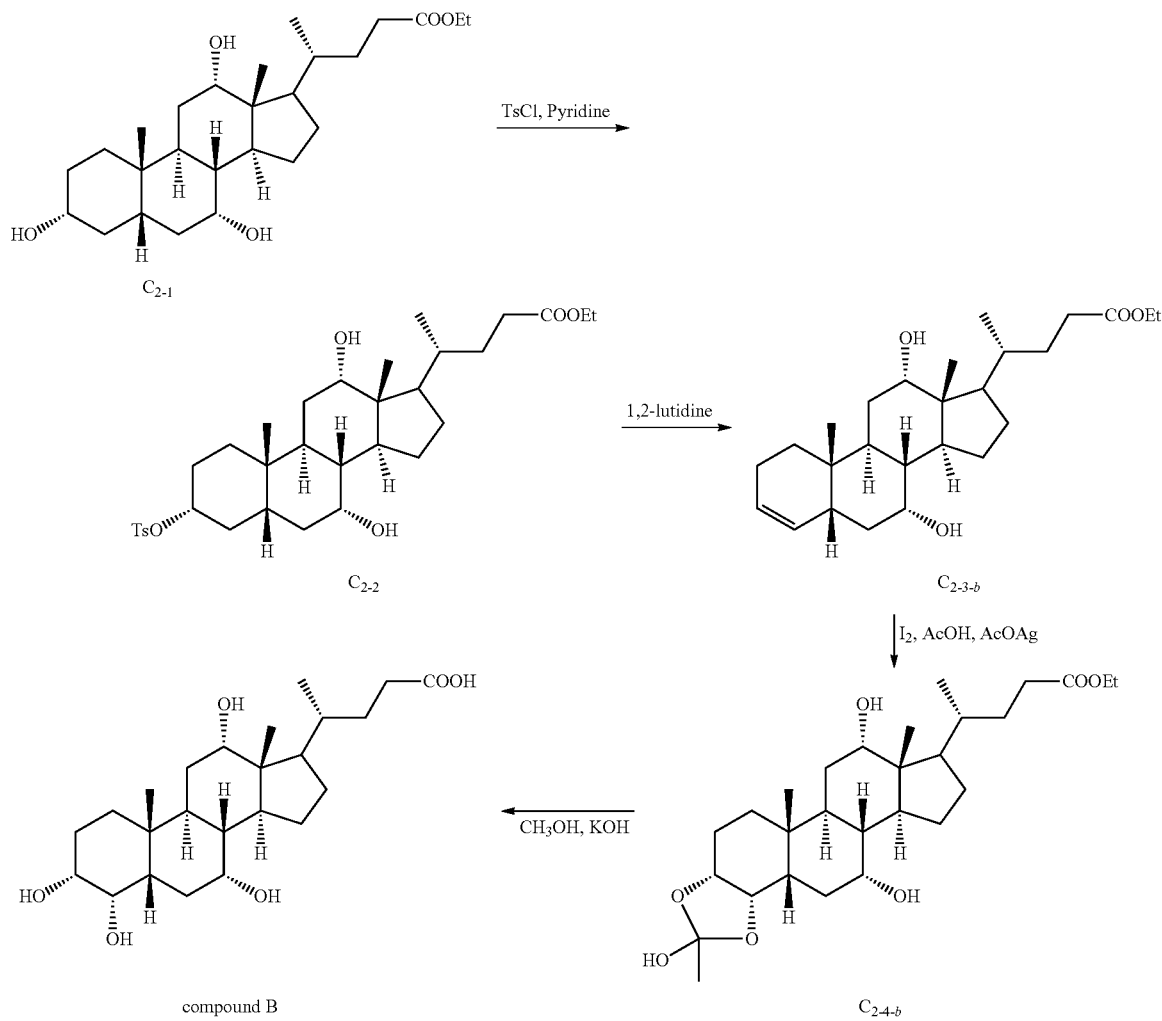

7. van Mil, S. W., Klomp, L. W., Bull, L. N. & Houwen, R. H. (2001) *Semin Liver Dis* 21, 535-44.

REFERENCES

1. Strautnieks, S. S., Bull, L. N., Knisely, A. S., Kocoshis, S. A., Dahl, N., Arnell, H., Sokal, E., Dahan, K., Childs, S., Ling, V., Tanner, M. S., Kagalwalla, A. F., Nemeth, A., Pawlowska, J., Baker, A., Mieli-Vergani, G., Freimer, N. B., Gardiner, R. M. & Thompson, R. J. (1998) *Nat Genet.* 20, 233-8.
2. Jansen, P. L., Strautnieks, S. S., Jacquemin, E., Hadchouel, M., Sokal, E. M., Hooiveld, G. J., Koning, J. H., De Jager-Krikken, A., Kuipers, F., Stellaard, F., Bijleveld, C. M., Gouw, A., Van Goor, H., Thompson, R. J. & Muller, M. (1999) *Gastroenterology* 117, 1370-9.
3. Fattinger, K., Funk, C., Pantze, M., Weber, C., Reichen, J., Stieger, B. & Meier, P. J. (2001) *Clin Pharmacol Ther* 69, 223-31.
4. Funk, C., Pantze, M., Jehle, L., Ponelle, C., Scheuermann, G., Lazendic, M. & Gasser, R. (2001) *Toxicology* 167, 83-98.
5. Funk, C., Ponelle, C., Scheuermann, G. & Pantze, M. (2001) *Mol Pharmacol* 59, 627-35.
6. Stieger, B., Fattinger, K., Madon, J., Kullak-Ublick, G. A. & Meier, P. J. (2000) *Gastroenterology* 118, 422-30.
8. Kubitz, R., Keitel, V., Scheuring, S., Kohrer, K. & Haussinger, D. (2006) *J Clin Gastroenterol* 40, 81-85.
9. Vallejo, M., Briz, O., Serrano, M. A., Monte, M. J. & Marin, J. J. (2006) *J Hepatol* 144, 1150-7.
10. Keitel, V., Vogt, C., Haussinger, D. & Kubitz, R. (2006) *Gastroenterology* 131, 624-9.
11. Green, R. M., Hoda, F. & Ward, K. L. (2000) *Gene* 241, 117-23.
12. Byrne, J. A., Strautnieks, S. S., Mieli-Vergani, G., Higgins, C. F., Linton, K. J. & Thompson, R. J. (2002) *Gastroenterology* 123, 1649-58.
13. Gerloff, T., Stieger, B., Hagenbuch, B., Madon, J., Landmann, L., Roth, J., Hofmann, A. F. & Meier, P. J. (1998) *J Biol Chem* 273, 10046-50.
14. Noe, J., Stieger, B. & Meier, P. J. (2002) *Gastroenterology* 123, 1659-66.
15. Gerloff, T., Meier, P. J. & Stieger, B. (1998) *Liver* 18, 306-12.
16. Wang, R., Lam, P., Liu, L., Forrest, D., Yousef, I. M., Mignault, D., Phillips, M. J. & Ling, V. (2003) *Hepatology* 38, 1489-99.
17. Stieger, B., O'Neill, B. & Meier, P. J. (1992) *Biochem J* 284 (Pt 1), 67-74.

18. Wang, R., Salem, M., Yousef, I. M., Tuchweber, B., Lam, P., Childs, S. J., Helgason, C. D., Ackerley, C., Phillips, M. J. & Ling, V. (2001) *Proc Natl Acad Sci USA* 98, 2011-6.
19. Lam, P., Wang, R. & Ling, V. (2004) in *Falk Symposium No 141. XVIII International Bile Acid Meeting: Bile Acid Biology and its Therapeutic Implications* (Kluwer Academic, Dordrecht).
20. Lam, P., Wang, R. & Ling, V. (2005) *Biochemistry* 44, 12598-605.
21. Asamoto, Y., Tazuma, S., Ochi, H., Chayama, K. & Suzuki, H. (2001) *Biochem J* 359, 605-10.
22. Schinkel, A. H., Mayer, U., Wagenaar, E., Mol, C. A., van Deemter, L., Smit, J. J., van der Valk, M. A., Voordouw, A. C., Spits, H., van Tellingen, O., Zijlmans, J. M., Fibbe, W. E. & Borst, P. (1997) *Proc Natl Acad Sci USA* 94, 4028-33.
23. Hofmann, A. F. (1999) *Arch Intern Med* 159, 2647-58.
24. Hofmann, A. F. (2001) *Hepatology* 34, 848-50.
25. Tsukada, N., Azuma, T. & Phillips, M. J. (1994) *Proc Natl Acad Sci USA* 91, 6919-23.
26. Chen, H. L., Chen, H. L., Liu, Y. J., Feng, C. H., Wu, C. Y., Shyu, M. K., Yuan, R. H. & Chang, M. H. (2005) *J Hepatol* 43, 472-7.
27. Knisely, A. S. (2000) *Pediatr Dev Pathol* 3, 113-25.
28. Jacquemin, E. (2000) *Clin Liver Dis* 4, 753-63.
29. Matoba, N., Mosbach, E. H., Cohen, B. I., Une, M. & McSherry, C. K. (1989) *J Lipid Res* 30, 1005-14.
30. Kihira, K., Yoshii, M., Okamoto, A., Ikawa, S., Ishii, H. & Hoshita, T. (1990) *J Lipid Res* 31, 1323-6.
31. Kakiyama, G., Iida, T., Yoshimoto, A., Goto, T., Mano, N., Goto, J., Nambara, T., Hagey, L. R. & Hofmann, A. F. (2004) *J Lipid Res* 45, 567-73.
32. Shapiro, A. B., Corder, A. B. & Ling, V. (1997) *Eur J Biochem* 250, 115-21.
33. Shapiro, A. B., Fox, K., Lam, P. & Ling, V. (1999) *Eur J Biochem* 259, 841-50.
34. Shapiro, A. B. & Ling, V. (1997) *Eur J Biochem* 250, 130-7.
35. Takikawa, H., Sano, N., Also, M., Takamori, Y. & Yamanaka, M. (1997) *J Gastroenterol Hepatol* 12, 84-6.
36. Wang, R., Chen, H.-L., Liu, L., Sheps, J. A., Low, C., Phillips, M. J. & Ling, V. (2007).
37. Rust C, Karnitz L M, Paya C V, Moscat J, Simari R D, Gores G J. J Biol. Chem. 2000; 275:20210-20216
38. Sodeman T, Bronk S F, Roberts P J, Miyoshi H, Gores G J. Am. J Physiol Gastrointest Liver Physiol. 2000; 278: G992-G999
39. Jones B A, Rao Y P, Stravitz R T, Gores G J. Am. J. Physiol. 1997; 272:G1109-G1115
40. Kwo P, Patel T, Bronk S F, Gores G J. Am. J. Physiol. 1995; 268:G613-G621
41. Rodrigues C M, Fan G, Ma X, Kren B T, Steer C J. J Clin Invest. 1998; 101:2790-2799
42. Wang H, Chen J, Hollister K, Sowers L C, Forman B M. Mol. Cell. 1999; 3:543-553
43. Makishima M, Okamoto A Y, Repa J J, Tu H, Learned R M, Luk A, Hull M V, Lustig K D, Mangelsdorf D J, Shan B. Science. 1999; 284:1362-1365
44. Chiang J Y, Kimmel R, Weinberger C, Stroup D. J Biol. Chem. 2000; 275:10918-10924
45. Parks D J, Blanchard S G, Bledsoe R K, Chandra G, Consler T G, Kliewer S A, Stimmel J B, Willson T M, Zavacki A M, Moore D D, et al. Science. 1999; 284:1365-1368
46. Goodwin B, Jones S A, Price R R, Watson M A, McKee D D, Moore L B, Galardi C, Wilson J G, Lewis M C, Roth M E, et al. Mol. Cell. 2000; 6:517-526
47. Sinal C J, Tohkin M, Miyata M, Ward J M, Lambert G, Gonzalez F J. Cell. 2000; 102:731-744
48. Hofmann A F. J Pediatr Gastroenterol Nutr, 1995; 20(4): 376 90
49. Jansen P L and Sturm E. Liver Int 2003; 23(5):315-22
50. Childs, S.; Ling V. Important Adv Oncol. 1994; 21-36
51. Hofmann A F, Sjovall J, Kurz G, Radominska A, Schteingart C D, Tint G S, Vlahcevic Z R, Setchell K D. J Lipid Res. 1992; 33(4):599-604.
52. Tohma, M, Mahara R, Takeshita H, Kurosawa T, Ikegawa S, Nittono H. Chem. Pharm. Bull. 1985; 33(7):3071-3073
53. Iida T, Tamaru T, Chang F C, Goto J, Nambara T. Journal of Lipid Research 1991; 32:649-658
54. Iida T, Komatsubara I, Chang F C, Goto J, Nambara T. Steroids 1991; 56:114-122
55. Aggarwal S K, Batta A K, Salen G, Shefer S. Steroids 1992; 57:107-111
56. Iida T, Nishida S, Chang F C, Niwa T, Goto J, Nambara T. Steroids 1993; 58:148-152
57. Kurosawa T, Nakano H, Sato M, Tohma M. Steroids 1995; 60:439-444
58. Kurosawa T, Sato M, Nakano H, Tohma M. Steroids 1996; 61:421-428
59. Iida T, Hikosaka M, Kakiyama G, Shiraishi K, Schteingart C D, Hagey L R, Ton-Nu H T, Hofmann A F, Mano N, Goto J, Nambara T. Chem. Pharm. Bull. 2002; 50(10):1327-1334
60. Bohme, M., Muller, M., Leier, I., Jedlitschky, G. and Keppler, D. (1994) Cholestasis caused by inhibition of the adenosine triphosphate-dependent bile salt transport in rat liver. Gastroenterology 107, 255-265
61. Iida, T.; Komatsubara, I.; Yoda, S.; Goto, J.; Nambara, T.; Chang, F. C. *Steroids* 1990, 55, 531-539.62. Aggarwal, S. K.; Batta, A. K.; Salen, G.; Shefer, S. *Steroids* 1992, 57, 107-111.
63. Wang, R., et al., *Severe cholestasis induced by cholic acid feeding in knockout mice of sister of P-glycoprotein*. Hepatology, 2003. 38(6): p. 1489-99.
64. Wang, R., et al., *Targeted inactivation of sister of P-glycoprotein gene (spgp) in mice results in nonprogressive but persistent intrahepatic cholestasis*. Proc Natl Acad Sci USA, 2001. 98(4): p. 2011-6.
65. Forrest, D. N., Bile Salt Hydroxylation as a mechanism for detoxification in spgp knockout mice. M. Sc. Thesis, University of British Columbia, 2003.
66. Gouin, S.; Zhu, X. X. Synthesis of 3!- and 3"-dimers from selected bile acids. Steroids 1996, 61, 664-669.
67. Fieser, L. F.; Rajagopalan, S. Selective oxidation with N-bromosuccinimide. I. Cholic acid. J. Am. Chem. Soc. 1949, 71, 3609-3614.
68. Pütz, G.; Schmide,r W.; Nitschk,e R.; Kurz, G.; Blum, H. E. Synthesis of phospholipid-conjugated bile salts and interaction of bile salt-coated liposomes with cultured hepatocytes. J. Lipid Res. 2005, 46, 2325-2338.
69. S, Narasimhan* and R. Balakumar Synthetic Applications of Zinc Borohydride, Aldrichmica acta, Vol. 31, No. 1, 1998 19
70. Paul L. Ornatein,* M. Brian Arnold, Nancy K. Augenstein, and Jonathan W. Pascha, Syntheses of 6-Oxodecahydroisoquinoline-3-carboxylates. Useful Intermediates for the Preparation of Conformationally Defined Excitatory Amino Acid Antagonists, J. Org. Chem., Vol. 56, No. 14, 1991 4389
71. Rossi, S. S., et al. "High pressure liquid chromatographic analysis of conjugated bile acids in human bile: simultaneous resolution of sulfated and unsulfated lithocholyl amidates and the common conjugated bile acids." 1987. *J Lipid Res* 28(5): 589-95

72. Hagey, L. R., et al. "An N-acyl glycyltaurine conjugate of deoxycholic acid in the biliary bile acids of the rabbit." 1998. *J Lipid Res* 39(11): 2119-24.

73. Chen H L, et al. Progressive familial intrahepatic cholestasis with high gamma-glutamyltranspeptidase levels in Taiwanese infants: role of MDR3 gene defect? 2001. *Pediatr Res.* 50:50-5.

74. Tserng K Y and Klein P D. "Formylated bile acids: improved synthesis, properties, and partial deformylation." 1977 Steroids, 29: 635-648

75. Leppik R A. "Improved synthesis of 3-keto, 4-ene-3-keto, and 4,6-diene-3-keto bile acids." 1983 Steroids, 41: 475-484

76. Iida T. et al. "Potential bile acid metabolites. 17. Synthesis of 2 beta-hydroxylated bile acids." 1991 Steroids, 56: 114-122

77. Iida T. et al. "Potential bile acid metabolites. 116. Synthesis of stereoisomeric 3 alpha, 6,7,12 alpha-tetrahydroxy-5 beta-cholanoic acids."1990 Steroids, 55: 530-539.

OTHER EMBODIMENTS

The present invention has been described with regard to one or more embodiments. However, it will be apparent to persons skilled in the art that a number of variations and modifications can be made without departing from the scope of the invention as defined in the claims. Therefore, although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to," and the word "comprises" has a corresponding meaning. Citation of references herein shall not be construed as an admission that such references are prior art to the present invention. All publications are incorporated herein by reference as if each individual publication was specifically and individually indicated to be incorporated by reference herein and as though fully set forth herein. The invention includes all embodiments and variations substantially as hereinbefore described and with reference to the examples and drawings.

What is claimed is:

1. A method of stimulating bile flow in a subject having a biliary disorder, the method comprising administering a therapeutically effective amount of a compound according to Formula I:

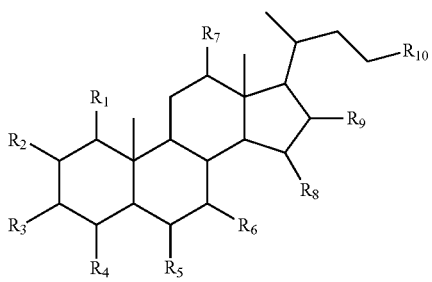

or a salt, ester, enol ether, enol ester, solvate, or hydrate thereof or is a tauryl or glycyl conjugate thereof, wherein any one of $R_1$ to $R_9$ may be —H or —OH, provided that at least four of $R_1$ to $R_9$ are —OH;
and
$R_{10}$ may be —COOH or —CH$_2$OH.

2. The method of claim 1 wherein said compound comprises a hydrophilicity greater than that of cholate.

3. The method of claim 1 wherein said compound is selected from the group consisting of a tetrahydroxylated bile acid and a pentahydroxylated bile acid.

4. The method of claim 3 wherein said tetrahydroxylated bile acid is selected from the group consisting of:
a 3,6,7,12-tetrahydroxycholanoic acid,
a 3,4,7,12-tetrahydroxycholanoic acid,
a 1,3,7,12-tetrahydroxycholanoic acid, and
a 2,3,7,12-tetrahydroxycholanoic acid.

5. The method of claim 4 wherein said 3,6,7,12-tetrahydroxycholanoic acid is selected from the group consisting of:
3α, 6α, 7α, 12α-tetrahydroxy-5β-cholan-24-oic acid,
3α, 6β, 7α, 12α-tetrahydroxy-5β-cholan-24-oic acid,
3α, 6α, 7β, 12α-tetrahydroxy-5β-cholan-24-oic acid,
3α, 6β, 7β, 12α-tetrahydroxy-5β-cholan-24-oic acid,
3α, 6α, 7α, 12β-tetrahydroxy-5β-cholan-24-oic acid,
3α, 6β, 7α, 12β-tetrahydroxy-5β-cholan-24-oic acid, and
3α, 6β, 7β, 12β-tetrahydroxy-5β-cholan-24-oic acid,
or wherein said 2,3,7,12-tetrahydroxycholanoic acid is 2α,3α,7α,12α-tetrahydroxy-5β-cholanoic acid,
or wherein said 3,4,7,12-tetrahydroxycholanoic acid is 3α,4α,7α,12α-tetrahydroxy-5β-cholanoic acid.

6. The method of claim 1 wherein said compound has a preferential affinity for MDRI when compared to BSEP.

7. The method of claim 1 wherein said compound has a high affinity for MDRI.

8. The method of claim 1 wherein said compound is selected from the group consisting of
a tauryl or glycyl conjugate of a 3α, 6β, 7α, 12β-tetrahydroxy-5β-cholan-24-oic acid, a tauryl or glycyl conjugate of a 3α, 6β, 7β, 12β-tetrahydroxy-5β-cholan-24-oic acid, and a tauryl conjugate of a 3α, 6β, 7α, 12α-tetrahydroxy-5β-cholan-24-oic acid.

9. The method of claim 1 wherein said compound is a tauryl conjugate of a 3α, 6β, 7β, 12α-tetrahydroxy-5β-cholan-24-oic acid.

10. The method of claim 1 further comprising administering at least one other therapeutic agent.

11. The method of claim 10 wherein said other therapeutic agent has a preferential affinity for BSEP.

12. The method of claim 10 wherein said other therapeutic agent is ursodeoxycholate.

13. The method of claim 1 wherein said biliary disorder arises from bile deficiency, bile toxicity or impaired liver function.

14. The method of claim 1 wherein said subject is a human.

15. The method of claim 4 wherein said 2,3,7,12-tetrahydroxycholanoic acid is a 2α,3α,7α,12α-tetrahydroxy-5β-cholanoic acid.

16. The method of claim 4 wherein said 3,4,7,12-tetrahydroxycholanoic acid is a 3α,4α,7α,12α-tetrahydroxy-5β-cholanoic acid.

17. The method of claim 1 wherein said biliary disorder is benign biliary strictures, benign pancreatic disease cysts, liver fibrosis, liver damage, common bile duct stones, pancreatitis, pancreatic cancer or pseudocyst, periampullary cancer, bile duct carcinoma, primary sclerosing cholangitis, autoimmune cholangitis, extrinsic duct compression, viral hepatitis, drug-induced idiosyncratic hepatotoxicity, primary biliary cirrhosis, primary sclerosing cholangitis, alcoholic hepatitis with or without cirrhosis, nonalcoholic steatohepatitis, non-alcoholic fatty liver disease, chronic hepatitis with or without cirrhosis, intrahepatic cholestasis of pregnancy, biliary calculosis, biliary dyscinesia, acute liver failure, αl-antitrypsin deficiency, PFIC2, Benign Recurrent Intrahepatic Cholestasis, portal hypertension, or hepatic vein thrombosis, or is cholestasis arising from diverticulitis, sepsis, bacterial abscess, use of drugs, lymphoma, tuberculosis, metastatic carcinoma, sarcoidosis, amyloidosis, intravenous feeding, Sjogren syndrome, Wilson's disease, ischemia, toxins, alcohol, hepatocellular carcinoma, or veno-occlusive disease.

18. The method of claim 4 wherein said 3,6,7,12-tetrahydroxycholanoic acid is 3α, 6α, 7α, 12α-tetrahydroxy-5β-cholan-24-oic acid.

* * * * *